US008119351B2

(12) United States Patent
Vincent et al.

(10) Patent No.: US 8,119,351 B2

(45) Date of Patent: Feb. 21, 2012

(54) CC2D2A GENE MUTATIONS ASSOCIATED WITH JOUBERT SYNDROME AND DIAGNOSTIC METHODS FOR IDENTIFYING THE SAME

(75) Inventors: John B. Vincent, Toronto (CA); Muhammad Ayub, Durham (GB)

(73) Assignee: Centre for Addiction and Mental Health, Toronto, Ontario (CA)

( * ) Notice: Subject to any disclaimer, the term of this patent is extended or adjusted under 35 U.S.C. 154(b) by 0 days.

(21) Appl. No.: 12/681,347

(22) PCT Filed: Oct. 3, 2008

(86) PCT No.: PCT/CA2008/001760

§ 371 (c)(1), (2), (4) Date: Jul. 15, 2010

(87) PCT Pub. No.: WO2009/043173

PCT Pub. Date: Apr. 9, 2009

(65) Prior Publication Data

US 2010/0297636 A1 Nov. 25, 2010

Related U.S. Application Data

(60) Provisional application No. 60/977,803, filed on Oct. 5, 2007.

(51) Int. Cl.
*C12Q 1/68* (2006.01)

(52) U.S. Cl. ..................................... 435/6.11; 435/6.16

(58) Field of Classification Search ........................ None
See application file for complete search history.

(56) References Cited

U.S. PATENT DOCUMENTS

2007/0015194 A1 1/2007 Shohat et al. ..................... 435/6
2007/0099251 A1 5/2007 Zhang et al. ................. 435/7.23

FOREIGN PATENT DOCUMENTS

WO WO 2007/047796 A2 4/2007

OTHER PUBLICATIONS

Written Opinion and International Search Report for International Application No. PCT/CA2008/001760, mailed Jan. 21, 2009.
Basel-Vanagaite L. et al., "The CC2D1A, a Member of a New Gene Family with C2 Domains, is Involved in Autosomal Recessive Non-Syndromic Mental Retardation", J. Med. Genet, vol. 43, pp. 203-210 (2006).
Cantagrel V. et al., "Mutations in the Cilia Gene ARL13B Lead to the Classical Form of Joubert Syndrome", The American Journal of Human Genetics, vol. 83, pp. 170-179 (2008).
Chelly J. et al., "Genetics and Pathology of Mental Retardation", European Journal of Human Genetics, vol. 14, pp. 701-713 (2006).
Curry C.J.. "Rational Evaluation of the Adolescent with Mental Retardation", Adolescent Medicine: State of the Art Reviews, vol. 13, No. 2, pp. 331-344 (2002).
Higgins J. J. et al., "A Mutation in a Novel ATP-Dependent Lon Protease Gene in a Kindred with Mild Mental Retardation", Neurology, vol. 63, pp. 1927-1931 (2004).
Joubert M, M.D. et al., "Familial Agenesis of the Cerebellar Vermis", Neurology, vol. 19, pp. 813-825 (1969).
Maria, Bernard L. et al., "Clinical Features and Revised Diagnostic Criteria in Joubert Syndrome" Journal of Child Neurology, vol. 14, No. 9, pp. 583-590, (1999).
Molinari F. et al., "Truncating Neurotrypsin Mutation in Autosomal Recessive Nonsyndromic Mental Retardation", Science, vol. 298, pp. 1179-1781 (2002).
Murphy, C. C. et al., "Epidemiology of Mental Retardation in Children", Mental Retardation and Developmental Disabilities Research Reviews, vol. 4, pp. 6-13 (1998).
Najmabadi H. et al., "Homozygosity Mapping in Consanguineous Families Reveals Extreme Heterogeneity of Non-Syndromic Autosomal Recessive Mental Retardation and Identifies 8 novel Gene Loci", Hum Genet, vol. 121, pp. 43-48 (2007).
Noor, A. et al., "CCD2A, Encoding A Coiled-Coil and C2 Domain Protein, Causes Autosomal-Recessive Mental Retardation with Retinitis Pigmentosa", The American Journal of Human Genetics, vol. 82, pp. 1011-1018 (2008).
Parisi, M. MD, Ph.D. et al., "Joubert Syndrome", Gene Reviews, http://74.125.47.132/search?q=cache:kEWvPJa9r_ IJ:www.ncbi.nlm.nih.gov/bookshelf, (2010).
Parisi,, M. MD, Ph.D. et al., "Joubert Syndrome (and Related Disorders) (OMIM 213300)", European Journal of Human Genetics, vol. 15, pp. 511-521 (2007).
Shea, S., "Mental Retardation in Children Ages 6 to 16", Elsevier, Seminars in Pediatric Neurology, pp. 262-270 (2006).
Tallila, J. et al., "Identification of CC2D2A as a Meckel Syndrome Gene Adds an Important Piece to the Ciliopathy Puzzle", The American Journal of Human Genetics, vol. 82, pp. 1362-1367 (2008).
Uyguner O. et al., "A New Locus for Autosomal Recessive Non-Syndromic Mental Retardation Maps to 1p21.1-p13.3", Clin. Genet., vol. 71, pp. 212-219 (2007).
Database Genbank [Online], "Homo Sapiens KIAA1345 Protein (KIAA1345), mRNA", retrieved from NCBI accession No. NM_001080522, (2007).
Bernet, W. et al., Section Editors,"Practice Parameters for the Assessment and Treatment of Children, Adolescent and Adults with Mental Retardaticn and Comorbid Mental Disorders", Journal of the American Academy of Child & Adolescent Psychiatry, vol. 38, No. 12 (1999).

*Primary Examiner* — John Ulm

(74) *Attorney, Agent, or Firm* — Winston & Strawn LLP

(57) ABSTRACT

The present invention provides a method of screening a subject for mutations in the CC2D2A gene that are associated with Joubert syndrome, an autosomal recessive form of mental retardation. The present invention also provides proteins that are associated with Joubert syndrome including proteins comprising an amino acid sequence that terminates in DHEGGSGMES (SEQ ID NO: 1). Also provided are nucleotide sequences encoding such proteins and methods of screening subjects to identify nucleotide sequences or proteins associated with Joubert syndrome.

21 Claims, 11 Drawing Sheets

Figure 1A

MNPREEKVKIITEEFIENDEDADMGRQNKNSKVRRQPRKKQPPTAVPKEMVSEKSHLGNPQEPVQEEPKTR
LLSMTVRRGPRSLPPIPSTSRTGFAEFSMRGRMREKLQAARSKAESALLQEIPTPRPRRLRSPSKKELETEFGT
EPGKEVERTQQEVDSQSYSRVKFHDSARKIKPKPQVPPGFPSAEEAYNFFTFNFDPEPEGSEEKPKARHRAG
TNQEEEEGEEEEPPAQGGGKEMDEEELLNGDDAEDFLLGLDHVADDFVAVRPADYESIHDRLQMEREMLFI
PSRQTVPTYKKLPENVQPRFLEDEGLYTGVRPEVARTNQNIMENRLLMQDPERRWFGDDGRILALPNPIKPF
PSRPPVLTQEQSIKAELETLYKKAVKYVHSSQHVIRSGDPPGNFQLDIDISGLIFTHHPCFSREHVLAAKLAQL
YDQYLARHQRNKAKFLTDKLQALRNAVQTGLDPEKPHQSLDTIQKTINEYKSEIRQTRKFRDAEQEKDRTL
LKTIIKVWKEMKSLREFQRFTNTPLKLVLRKEKADQKADEEAYEAEIQAEISELLEEHTEEYAQKMEEYRTS
LQQWKAWRKVQRAKKKKRKQAAEEHPGDEIAEPYPEEDLVKPSPPEPTDRAVIEQEVRERAAQSRRRPWE
PTLVPELSLAGSVTPNDQCPRAEVSRREDVKKRSVYLKVLFNNKEVSRTVSRPLGADFRVHFGQIFNLQIVN
WPESLTLQVYETVGHSSPTLLAEVFLPIPETTVVTGRAPTEEVEFSSNQHVTLDHEGVGSGMES

(SEQ ID NO:3; Full length truncation protein)

Figure 1B

NPREEKVKIITEEFIENDEDADMGRQNKNSKVRRQPRKKQPPTAVPKEMVSEKSHLGNPQEPVQEEPKTRLL
SMTVRRGPRSLPPIPSTSRTGFAEFSMRGRMREKLQAARSKAESALLQEIPTPRPRRLRSPSKKELETEFGTEP
GKEVERTQQEVDSQSYSRVKFHDSARKIKPKPQVPPGFPSAEEAYNFFTFNFDPEPEGSEEKPKARHRAGTN
QEEEEGEEEEPPAQGGGKEMDEEELLNGDDAEDFLLGLDHVADDFVAVRPADYESIHDRLQMEREMLFIPS
RQTVPTYKKLPENVQPRFLEDEGLYTGVRPEVARTNQNIMENRLLMQDPERRWFGDDGRILALPNPIKPFPS
RPPVLTQEQSIKAELETLYKKAVKYVHSSQHVIRSGDPPGNFQLDIDISGLIFTHHPCFSREHVLAAKLAQLY
DQYLARHQRNKAKFLTDKLQALRNAVQTGLDPEKPHQSLDTIQKTINEYKSEIRQTRKFRDAEQEKDRTLL
KTIIKVWKEMKSLREFQRFTNTPLKLVLRKEKADQKADEEAYEAEIQAEISELLEEHTEEYAQKMEEYRTSL
QQWKAWRKVQRAKKKKRKQAAEEHPGDEIAEPYPEEDLVKPSPPEPTDRAVIEQEVRERAAQSRRRPWEP
TLVPELSLAGSVTPNDQCPRAEVSRREDVKKRSVYLKVLFNNKEVSRTVSRPLGADFRVHFGQIFNLQIVNW
PESLTLQVYETVGHSSPTLLAEVFLPIPETTVVTGRAPTEEVEFSSNQHVTLDHEGVGSGMES

(SEQ ID NO:4; full length truncation protein with N-terminal methionine removed)

Figure 1C

```
   1 cttttgtaaa gtttcttaag ctatattcta atggatatgg gctgacatta acaaggaccc
  61 atcccagcca aaatgaatcc cagggaagaa aaagtaaaaa taattacaga ggagttcatt
 121 gaaaatgatg aggatgcaga catgggaaga cagaataaga actcaaaggt tcgaagacag
 181 ccaagaaaga aacagccacc aactgctgtc cccaaggaaa tggtgtccga aaaatcccac
 241 cttggcaacc cccaggagcc tgtgcaggag gagcccaaga cccgcctcct gagtatgaca
 301 gtccggagag gcccacggag cttacctcca attccttcaa cttccagaac aggctttgca
 361 gaattttcca tgaggggacg catgagggag aaattgcaag cagcgaggtc caaagcagaa
 421 agtgcattgc tgcaggaaat ccccactcct cggcccagac gcttacgaag tcccagtaag
 481 aaagaattgg agactgaatt tggcacagag ccagggaaag aggtagaaag gactcaacaa
 541 gaagttgact cccaaagtta ctcaagagtc aagttccatg attctgcacg aaaaatcaag
 601 cctaaacccc aggttccacc tggcttccct tctgcagaag aggcctataa cttctttact
 661 ttcaactttg atcccgaacc agaaggatca gaggaaaaac caaaagcaag acatagagcg
 721 ggaactaatc aagaggagga ggaagggaa gaagaagaac cacctgcaca aggaggagga
 781 aaggaaatgg atgaggaaga actgcttaat ggtgatgatg ccgaggactt cctattgggc
 841 ttagatcacg tggctgacga ttttgtagca gtcagacctg cagattatga aagcatccat
 901 gatcggctgc agatggaaag agaaatgctc ttcataccca gtaggcagac agtccctaca
 961 tataaaaagc ttcctgagaa tgtacagccc aggttcctgg aagatgaagg cctttacacc
1021 ggggtaagac cagaggtggc acgcaccaat cagaacatca tggagaacag attgctgatg
1081 caggaccccg aaagaagatg gtttggagat gacggcagga tcctagctct gccaaacccc
1141 atcaagccat ttccttcaag gccgccagta ctaacacagg agcagagcat taaggcagag
1201 cttgaaacac tgtataaaaa ggctgtaaaa tacgttcaca gtagtcagca tgtgatcaga
1261 tctggagacc ctcctggaaa tttccaactg gacattgata tttcagggtt aatcttcact
1321 catcatccct gttttagccg agagcatgtt ttggcagcca agctggccca gttatatgac
1381 cagtaccttg caagacacca gagaaacaag gcgaaatttc ttactgataa gctccaagct
```

1441 ttaagaaatg ctgttcagac tggccttgat ccagaaaaac ctcatcagtc tctcgatacc
1501 atccaaaaaa ccatcaatga gtataaatct gaaattcgac aaacaagaaa attccgtgat
1561 gctgaacaag aaaaagatag aacattgctt aagactatca taaaagtttg gaaagagatg
1621 aaatcccttc gagagttcca gagatttaca aatactccct tgaaacttgt tttgagaaag
1681 gaaaaagctg accagaaagc agatgaagaa gcatatgaag cagaaattca agctgaaata
1741 agtgaactgt tagaagagca cacggaggag tacgcacaga agatggaaga atacagaacg
1801 tcgttacaac agtggaaggc ctggaggaaa gtgcaaaggg ccaagaagaa gaaaaggaaa
1861 caagcagcag aagaacatcc cggtgatgag attgcagagc cgtatcccga ggaggacctt
1921 gtgaagccca gccctccaga gcccactgat cgggcagtga tagagcagga ggtgagggag
1981 agagcagccc agagcaggag gaggccttgg gagcccacgc tggtcccgga gctaagcctg
2041 gcaggaagcg taacacccaa tgaccagtgc cccagagcgg aggtctcgag aagggaggat
2101 gtaaagaagc gctcagtgta cttaaaagtg ctgttcaaca acaaggaggt gtccaggaca
2161 gtcagtcggc cactaggagc agacttccga gttcactttg ggcagatttt caatttgcaa
2221 atagtcaact ggccggagag tttaacactt caggtctatg aaactgtcgg acacagtagt
2281 cccaccttgc tagcagaagt gtttctgcct attcctgaga ctactgttgt cactggaagg
2341 gctcctactg aagaagtgga gtttagcagt aatcagcatg tgacactgga ccacgaggga
2401 gttggaagtg gtatggaaag ctaa SEQ ID No:5 (Representative DNA encoding mutant truncation protein 73-2424)

FIGURE 1D

1 cttttgtaaa gtttcttaag ctatattcta atggatatgg gctgacatta acaaggaccc
61 atcccagcca aaatgaatcc cagggaagaa aaagtaaaaa taattacaga ggagttcatt
121 gaaaatgatg aggatgcaga catgggaaga cagaataaga actcaaaggt tcgaagacag
181 ccaagaaaga aacagccacc aactgctgtc cccaaggaaa tggtgtccga aaaatcccac
241 cttggcaacc cccaggagcc tgtgcaggag gagcccaaga cccgcctcct gagtatgaca
301 gtccggagag gcccacggag cttacctcca attccttcaa cttccagaac aggctttgca
361 gaattttcca tgaggggacg catgagggag aaattgcaag cagcgaggtc caaagcagaa
421 agtgcattgc tgcaggaaat ccccactcct cggcccagac gcttacgaag tcccagtaag
481 aaagaattgg agactgaatt tggcacagag ccagggaaag aggtagaaag gactcaacaa
541 gaagttgact cccaaagtta ctcaagagtc aagttccatg attctgcacg aaaaatcaag
601 cctaaacccc aggttccacc tggcttccct tctgcagaag aggcctataa cttctttact
661 ttcaactttg atcccgaacc agaaggatca gaggaaaaac caaaagcaag acatagagcg
721 ggaactaatc aagaggagga ggaaggggaa gaagaagaac cacctgcaca aggaggagga
781 aaggaaatgg atgaggaaga actgcttaat ggtgatgatg ccgaggactt cctattgggc
841 ttagatcacg tggctgacga ttttgtagca gtcagacctg cagattatga aagcatccat
901 gatcggctgc agatggaaag agaaatgctc ttcataccca gtaggcagac agtccctaca
961 tataaaaagc ttcctgagaa tgtacagccc aggttcctgg aagatgaagg cctttacacc
1021 ggggtaagac cagaggtggc acgcaccaat cagaacatca tggagaacag attgctgatg
1081 caggaccccg aaagaagatg gtttggagat gacggcagga tcctagctct gccaaacccc
1141 atcaagccat ttccttcaag gccgccagta ctaacacagg agcagagcat taaggcagag
1201 cttgaaacac tgtataaaaa ggctgtaaaa tacgttcaca gtagtcagca tgtgatcaga
1261 tctggagacc ctcctggaaa tttccaactg gacattgata tttcagggtt aatcttcact
1321 catcatccct gttttagccg agagcatgtt ttggcagcca agctggccca gttatatgac
1381 cagtaccttg caagacacca gagaaacaag gcgaaatttc ttactgataa gctccaagct
1441 ttaagaaatg ctgttcagac tggccttgat ccagaaaaac ctcatcagtc tctcgatacc
1501 atccaaaaaa ccatcaatga gtataaatct gaaattcgac aaacaagaaa attccgtgat
1561 gctgaacaag aaaaagatag aacattgctt aagactatca taaaagtttg gaaagagatg
1621 aaatcccttc gagagttcca gagatttaca aatactccct tgaaacttgt tttgagaaag
1681 gaaaaagctg accagaaagc agatgaagaa gcatatgaag cagaaattca agctgaaata
1741 agtgaactgt tagaagagca cacggaggag tacgcacaga agatggaaga atacagaacg
1801 tcgttacaac agtggaaggc ctggaggaaa gtgcaaaggg ccaagaagaa gaaaaggaaa
1861 caagcagcag aagaacatcc cggtgatgag attgcagagc cgtatcccga ggaggacctt
1921 gtgaagccca gccctccaga gcccactgat cgggcagtga tagagcagga ggtgagggag
1981 agagcagccc agagcaggag gaggccttgg gagcccacgc tggtcccgga gctaagcctg
2041 gcaggaagcg taacacccaa tgaccagtgc cccagagcgg aggtctcgag aagggaggat
2101 gtaaagaagc gctcagtgta cttaaaagtg ctgttcaaca acaaggaggt gtccaggaca
2161 gtcagtcggc cactaggagc agacttccga gttcactttg ggcagatttt caatttgcaa
2221 atagtcaact ggccggagag tttaacactt caggtctatg aaactgtcgg acacagtagt
2281 cccaccttgc tagcagaagt gtttctgcct attcctgaga ctactgttgt cactggaagg

```
2341 gctcctactg aagaagtgga gtttagcagt aatcagcatg tgacactgga ccacgaggga
2401 gttggaagtg gagtgccctt ctcatttgaa gctgatggca gtaaccagct gactctgatg
2461 acctcaggga aagtgtctca tagtgtggca tgggccattg gagaaaacgg gataccttta
2521 attcctccat tgtcacagca gaacatcgga tttcggagtg ctttgaagaa agcagatgcc
2581 atctcatcta ttggcacatc aggactgaca gacatgaaaa aattggccaa gtgggcagca
2641 gagtccaagc tcgacccaaa tgaccccaac aatgcccctt tgatgcagct tatctcggtt
2701 gctaccagtg gtgaatccta tgtccctgat ttctttagac tggagcagct gcaacaggag
2761 tttaactttg tttcagatca agaattaaat agatccaaac gatttaggct tcttcatctt
2821 agaagccaag aggtgccaga attccgaaat tataagcaag ttccagtcta tgaccgagaa
2881 attatggaaa aggtattcca ggactatgag aaacggttac gagacagaaa tgtaatagaa
2941 accaaggaac acatagacac ccatagggcc atagtagcca agtacctcca gcaggttaga
3001 gaatcagtga taaatcgttt cttaattgca aaacaatatt ttcttcttgc tgatatgata
3061 gtagaagaag aagttcccaa tatcagcatt ttgggcctaa gcctttttcaa gctggcagaa
3121 caaaagcgac cactgcggcc aaggagaaaa ggtcggaaga aggtgacagc ccaaaacctg
3181 tctgatggag acataaagct gctggtgaac attgtgcgag cttacgacat tccagtgagg
3241 aagccggcag tgagcaaatt ccagcagccg tcgaggtctt caaggatgtt cagtgaaaag
3301 catgctgctt ccccaagcac gtacagccca acccacaatg ctgactaccc cctcggccag
3361 gttttagtac gtccctttgt agaagtctct tttcaacgaa cagtttgcca tacgactacg
3421 gctgaaggac caaaccctag ctggaatgaa gaactagaac ttccatttag ggctcctaat
3481 ggagattata gcacagccag tctgcagtca gtgaaagatg ttgtgttcat taacattttt
3541 gatgaagtac tgcatgatgt cttagaggat gaccgtgaaa gaggaagtgg aatccatact
3601 cgtattgaga gacactggct gggatgtgtg aaaatgccat ttagcacaat atatttccaa
3661 gcaaggtttg agtctcagga agatgagaaa ttacttcaag caactgagaa gtttcaagct
3721 gaatgtgcct taaagtttcc aaatcgtcag tgccttacaa cagtaattga tataagcgga
3781 aaaactgttt ttatcacacg ttatctcaaa cctttaaacc ctcctcagga gctccttaat
3841 gtctacccca ataatctaca ggcaactgca gaactggtgg ctcgatatgt gtccttgatt
3901 cccttcttgc ctgacactgt ctcatttggt ggtatctgtg acctctggag cacatctgat
3961 caatttcttg atctcctggc aggggatgaa gaagaacatg cagtactatt gtgtaattac
4021 tttctgtctc tgggtaagaa ggcctggctg ttgatgggca atgctattcc tgagggtcca
4081 actgcctatg tgctaacttg ggagcaaggt cgttatttaa tatggaatcc ctgcagtgga
4141 catttttatg gacaatttga tacattctgt cccttgaaaa atgtgggctg tttaataggt
4201 cctgacaata tttggtttaa tattcaacga tatgaatctc cactaaggat aaattttgat
4261 gtcaccaggc ccaagctatg gaaatctttc ttttcaagaa gccttccata tcctggcctt
4321 tccagtgttc agcctgaaga gctaatttac cagcgctcag acaaagcagc tgcagctgag
4381 ctacaagaca ggattgaaaa aatactaaaa gaaaaaatca tggactggag gccacgccat
4441 ctgactcggt ggaataggta ttgtacctct actctgcgtc acttcttgcc tctgttagaa
4501 aaaagtcaag gagaagatgt agaagatgac cacagagcag aactgctaaa acagctggga
4561 gactacaggt tctctggatt tcctcttcac atgccttatt ctgaagtgaa gcctttaatt
4621 gacgctgtgt atagtactgg agtacataat attgatgttc ctaatgttga atttgcttta
4681 gctgtataca tacacccata ccccaaaaat gttttgtctg tttggatcta tgttgcctct
4741 cttatacgca acaggtaatt tttttcactg tactttctgt atcatgtaaa aactacactt
4801 aggatatgag aaaattttaa attatatgca tcacatcaga agaacatatt attggcaaat
4861 aataaaatta tcaactgttt tcaaactgtg
```

SEQ ID NO:6 Representative Nucleotide sequence encoding CC2D2A wild-type protein; Further information may be obtained from the known gene coordinates: chr4:15,079,620-15,212,278 according to the UCSC March 2006 genome assembly.

Figure 1E

```
MNPREEKVKIITEEFIENDEDADMGRQNKNSKVRRQPRKKQPPTAVPKEMVSEKSHLGNPQEPVQEEPKTRLLSMTVR
RGPRSLPPIPSTSRTGFAEFSMRGRMREKLQAARSKAESALLQEIPTPRPRRLRSPSKKELETEFGTEPGKEVERTQQ
EVDSQSYSRVKFHDSARKIKPKPQVPPGFPSAEEAYNFFTFNFDPEPEGSEEKPKARHRAGTNQEEEEGEEEEPPAQG
GGKEMDEEELLNGDDAEDFLLGLDHVADDFVAVRPADYESIHDRLQMEREMLFIPSRQTVPTYKKLPENVQPRFLEDE
GLYTGVRPEVARTNQNIMENRLLMQDPERRWFGDDGRILALPNPIKPFPSRPPVLTQEQSIKAELETLYKKAVKYVHS
SQHVIRSGDPPGNFQLDIDISGLIFTHHPCFSREHVLAAKLAQLYDQYLARHQRNKAKFLTDKLQALRNAVQTGLDPE
KPHQSLDTIQKTINEYKSEIRQTRKFRDAEQEKDRTLLKTIIKVWKEMKSLREFQRFTNTPLKLVLRKEKADQKADEE
AYEAEIQAEISELLEEHTEEYAQKMEEYRTSLQQWKAWRKVQRAKKKKRKQAAEEHPGDEIAEPYPEEDLVKPSPPEP
TDRAVIEQEVRERAAQSRRRPWEPTLVPELSLAGSVTPNDQCPRAEVSRREDVKKRSVYLKVLFNNKEVSRTVSRPLG
ADFRVHFGQIFNLQIVNWPESLTLQVYETVGHSSPTLLAEVFLPIPETTVVTGRAPTEEVEFSSNQHVTLDHEGVGSG
VPFSFEADGSNQLTLMTSGKVSHSVAWAIGENGIPLIPPLSQQNIGFRSALKKADAISSIGTSGLTDMKKLAKWAAES
```

KLDPNDPNNAPLMQLISVATSGESYVPDFFRLEQLQQEFNFVSDQELNRSKRFRLLHLRSQEVPEFRNYKQVPVYDRE
IMEKVFQDYEKRLRDRNVIETKEHIDTHRAIVAKYLQQVRESVINRFLIAKQYFLLADMIVEEEVPNISILGLSLFKL
AEQKRPLRPRRKGRKKVTAQNLSDGDIKLLVNIVRAYDIPVRKPAVSKFQQPSRSSRMFSEKHAASPSTYSPTHNADY
PLGQVLVRPFVEVSFQRTVCHTTTAEGPNPSWNEELELPFRAPNGDYSTASLQSVKDVVFINIFDEVLHDVLEDDRER
GSGIHTRIERHWLGCVKMPFSTIYFQARFESQEDEKLLQATEKFQAECALKFPNRQCLTTVIDISGKTVFITRYLKPL
NPPQELLNVYPNNLQATAELVARYVSLIPFLPDTVSFGGICDLWSTSDQFLDLLAGDEEEHAVLLCNYFLSLGKKAWL
LMGNAIPEGPTAYVLTWEQGRYLIWNPCSGHFYGQFDTFCPLKNVGCLIGPDNIWFNIQRYESPLRINFDVTRPKLWK
SFFSRSLPYPGLSSVQPEELIYQRSDKAAAAELQDRIEKILKEKIMDWRPRHLTRWNRYCTSTLRHFLPLLEKSQGED
VEDDHRAELLKQLGDYRFSGFPLHMPYSEVKPLIDAVYSTGVHNIDVPNVEFALAVYIHPYPKNVLSVWIYVASLIRN
R

SEQ ID NO:7 Representative Amino Acid Sequence of Wild Type CC2D2A protein(see NM_001080522 at NCBI for more information)

Prostate
Spleen
Pancreas
Kidney
Lung
Small Intestine
Colon
Skeletal Muscle
Ovary
Thymus
Heart
Liver

SEQUENCE LISTING

<160> NUMBER OF SEQ ID NOS: 13

<210> SEQ ID NO 1
<211> LENGTH: 10
<212> TYPE: PRT
<213> ORGANISM: Artificial Sequence
<220> FEATURE:
<223> OTHER INFORMATION: a protein comprising an amino acid sequence that terminates

<400> SEQUENCE: 1

```
Asp His Glu Gly Gly Ser Gly Met Glu Ser
1               5                   10
```

<210> SEQ ID NO 2
<211> LENGTH: 12
<212> TYPE: PRT
<213> ORGANISM: Artificial Sequence
<220> FEATURE:
<223> OTHER INFORMATION: a protein comprising an amino acid sequence that terminates

<400> SEQUENCE: 2

```
Thr Leu Asp His Glu Gly Gly Ser Gly Met Glu Ser
1               5                   10
```

<210> SEQ ID NO 3
<211> LENGTH: 783
<212> TYPE: PRT
<213> ORGANISM: Artificial Sequence
<220> FEATURE:
<223> OTHER INFORMATION: full length truncation protein

<400> SEQUENCE: 3

```
Met Asn Pro Arg Glu Glu Lys Val Lys Ile Ile Thr Glu Glu Phe Ile
1               5                   10                  15

Glu Asn Asp Glu Asp Ala Asp Met Gly Arg Gln Asn Lys Asn Ser Lys
            20                  25                  30

Val Arg Arg Gln Pro Arg Lys Lys Gln Pro Pro Thr Ala Val Pro Lys
        35                  40                  45

Glu Met Val Ser Glu Lys Ser His Leu Gly Asn Pro Gln Glu Pro Val
    50                  55                  60

Gln Glu Glu Pro Lys Thr Arg Leu Leu Ser Met Thr Val Arg Arg Gly
65                  70                  75                  80

Pro Arg Ser Leu Pro Pro Ile Pro Ser Thr Ser Arg Thr Gly Phe Ala
                85                  90                  95

Glu Phe Ser Met Arg Gly Arg Met Arg Glu Lys Leu Gln Ala Ala Arg
            100                 105                 110

Ser Lys Ala Glu Ser Ala Leu Leu Gln Glu Ile Pro Thr Pro Arg Pro
        115                 120                 125

Arg Arg Leu Arg Ser Pro Ser Lys Lys Glu Leu Glu Thr Glu Phe Gly
    130                 135                 140

Thr Glu Pro Gly Lys Glu Val Glu Arg Thr Gln Gln Glu Val Asp Ser
145                 150                 155                 160

Gln Ser Tyr Ser Arg Val Lys Phe His Asp Ser Ala Arg Lys Ile Lys
                165                 170                 175

Pro Lys Pro Gln Val Pro Pro Gly Phe Pro Ser Ala Glu Glu Ala Tyr
            180                 185                 190

Asn Phe Phe Thr Phe Asn Phe Asp Pro Glu Pro Glu Gly Ser Glu Glu
        195                 200                 205
```

```
Lys Pro Lys Ala Arg His Arg Ala Gly Thr Asn Gln Glu Glu Glu Glu
    210                 215                 220

Gly Glu Glu Glu Glu Pro Pro Ala Gln Gly Gly Gly Lys Glu Met Asp
225                 230                 235                 240

Glu Glu Glu Leu Leu Asn Gly Asp Asp Ala Glu Asp Phe Leu Leu Gly
                245                 250                 255

Leu Asp His Val Ala Asp Asp Phe Val Ala Val Arg Pro Ala Asp Tyr
            260                 265                 270

Glu Ser Ile His Asp Arg Leu Gln Met Glu Arg Glu Met Leu Phe Ile
        275                 280                 285

Pro Ser Arg Gln Thr Val Pro Thr Tyr Lys Lys Leu Pro Glu Asn Val
    290                 295                 300

Gln Pro Arg Phe Leu Glu Asp Glu Gly Leu Tyr Thr Gly Val Arg Pro
305                 310                 315                 320

Glu Val Ala Arg Thr Asn Gln Asn Ile Met Glu Asn Arg Leu Leu Met
                325                 330                 335

Gln Asp Pro Glu Arg Arg Trp Phe Gly Asp Asp Gly Arg Ile Leu Ala
            340                 345                 350

Leu Pro Asn Pro Ile Lys Pro Phe Pro Ser Arg Pro Pro Val Leu Thr
        355                 360                 365

Gln Glu Gln Ser Ile Lys Ala Glu Leu Glu Thr Leu Tyr Lys Lys Ala
    370                 375                 380

Val Lys Tyr Val His Ser Ser Gln His Val Ile Arg Ser Gly Asp Pro
385                 390                 395                 400

Pro Gly Asn Phe Gln Leu Asp Ile Asp Ile Ser Gly Leu Ile Phe Thr
                405                 410                 415

His His Pro Cys Phe Ser Arg Glu His Val Leu Ala Ala Lys Leu Ala
            420                 425                 430

Gln Leu Tyr Asp Gln Tyr Leu Ala Arg His Gln Arg Asn Lys Ala Lys
        435                 440                 445

Phe Leu Thr Asp Lys Leu Gln Ala Leu Arg Asn Ala Val Gln Thr Gly
    450                 455                 460

Leu Asp Pro Glu Lys Pro His Gln Ser Leu Asp Thr Ile Gln Lys Thr
465                 470                 475                 480

Ile Asn Glu Tyr Lys Ser Glu Ile Arg Gln Thr Arg Lys Phe Arg Asp
                485                 490                 495

Ala Glu Gln Glu Lys Asp Arg Thr Leu Leu Lys Thr Ile Ile Lys Val
            500                 505                 510

Trp Lys Glu Met Lys Ser Leu Arg Glu Phe Gln Arg Phe Thr Asn Thr
        515                 520                 525

Pro Leu Lys Leu Val Leu Arg Lys Glu Lys Ala Asp Gln Lys Ala Asp
    530                 535                 540

Glu Glu Ala Tyr Glu Ala Glu Ile Gln Ala Glu Ile Ser Glu Leu Leu
545                 550                 555                 560

Glu Glu His Thr Glu Glu Tyr Ala Gln Lys Met Glu Glu Tyr Arg Thr
                565                 570                 575

Ser Leu Gln Gln Trp Lys Ala Trp Arg Lys Val Gln Arg Ala Lys Lys
            580                 585                 590

Lys Lys Arg Lys Gln Ala Ala Glu Glu His Pro Gly Asp Glu Ile Ala
        595                 600                 605

Glu Pro Tyr Pro Glu Glu Asp Leu Val Lys Pro Ser Pro Pro Glu Pro
    610                 615                 620

Thr Asp Arg Ala Val Ile Glu Gln Glu Val Arg Glu Arg Ala Ala Gln
```

625 630 635 640

Ser Arg Arg Arg Pro Trp Glu Pro Thr Leu Val Pro Glu Leu Ser Leu
645 650 655

Ala Gly Ser Val Thr Pro Asn Asp Gln Cys Pro Arg Ala Glu Val Ser
660 665 670

Arg Arg Glu Asp Val Lys Lys Arg Ser Val Tyr Leu Lys Val Leu Phe
675 680 685

Asn Asn Lys Glu Val Ser Arg Thr Val Ser Arg Pro Leu Gly Ala Asp
690 695 700

Phe Arg Val His Phe Gly Gln Ile Phe Asn Leu Gln Ile Val Asn Trp
705 710 715 720

Pro Glu Ser Leu Thr Leu Gln Val Tyr Glu Thr Val Gly His Ser Ser
725 730 735

Pro Thr Leu Leu Ala Glu Val Phe Leu Pro Ile Pro Glu Thr Thr Val
740 745 750

Val Thr Gly Arg Ala Pro Thr Glu Glu Val Glu Phe Ser Ser Asn Gln
755 760 765

His Val Thr Leu Asp His Glu Gly Val Gly Ser Gly Met Glu Ser
770 775 780

<210> SEQ ID NO 4
<211> LENGTH: 782
<212> TYPE: PRT
<213> ORGANISM: Artificial Sequence
<220> FEATURE:
<223> OTHER INFORMATION: full length truncation protein with N-terminal methionine removed

<400> SEQUENCE: 4

Asn Pro Arg Glu Glu Lys Val Lys Ile Ile Thr Glu Glu Phe Ile Glu
1 5 10 15

Asn Asp Glu Asp Ala Asp Met Gly Arg Gln Asn Lys Asn Ser Lys Val
20 25 30

Arg Arg Gln Pro Arg Lys Lys Gln Pro Pro Thr Ala Val Pro Lys Glu
35 40 45

Met Val Ser Glu Lys Ser His Leu Gly Asn Pro Gln Glu Pro Val Gln
50 55 60

Glu Glu Pro Lys Thr Arg Leu Leu Ser Met Thr Val Arg Arg Gly Pro
65 70 75 80

Arg Ser Leu Pro Pro Ile Pro Ser Thr Ser Arg Thr Gly Phe Ala Glu
85 90 95

Phe Ser Met Arg Gly Arg Met Arg Glu Lys Leu Gln Ala Ala Arg Ser
100 105 110

Lys Ala Glu Ser Ala Leu Leu Gln Glu Ile Pro Thr Pro Arg Pro Arg
115 120 125

Arg Leu Arg Ser Pro Ser Lys Lys Glu Leu Glu Thr Glu Phe Gly Thr
130 135 140

Glu Pro Gly Lys Glu Val Glu Arg Thr Gln Gln Glu Val Asp Ser Gln
145 150 155 160

Ser Tyr Ser Arg Val Lys Phe His Asp Ser Ala Arg Lys Ile Lys Pro
165 170 175

Lys Pro Gln Val Pro Pro Gly Phe Pro Ser Ala Glu Glu Ala Tyr Asn
180 185 190

Phe Phe Thr Phe Asn Phe Asp Pro Glu Pro Glu Gly Ser Glu Glu Lys
195 200 205

Pro Lys Ala Arg His Arg Ala Gly Thr Asn Gln Glu Glu Glu Glu Gly

```
    210                 215                 220

Glu Glu Glu Glu Pro Pro Ala Gln Gly Gly Gly Lys Glu Met Asp Glu
225                 230                 235                 240

Glu Glu Leu Leu Asn Gly Asp Asp Ala Glu Asp Phe Leu Leu Gly Leu
                245                 250                 255

Asp His Val Ala Asp Asp Phe Val Ala Val Arg Pro Ala Asp Tyr Glu
            260                 265                 270

Ser Ile His Asp Arg Leu Gln Met Glu Arg Glu Met Leu Phe Ile Pro
        275                 280                 285

Ser Arg Gln Thr Val Pro Thr Tyr Lys Lys Leu Pro Glu Asn Val Gln
    290                 295                 300

Pro Arg Phe Leu Glu Asp Glu Gly Leu Tyr Thr Gly Val Arg Pro Glu
305                 310                 315                 320

Val Ala Arg Thr Asn Gln Asn Ile Met Glu Asn Arg Leu Leu Met Gln
                325                 330                 335

Asp Pro Glu Arg Arg Trp Phe Gly Asp Asp Gly Arg Ile Leu Ala Leu
            340                 345                 350

Pro Asn Pro Ile Lys Pro Phe Pro Ser Arg Pro Pro Val Leu Thr Gln
        355                 360                 365

Glu Gln Ser Ile Lys Ala Glu Leu Glu Thr Leu Tyr Lys Lys Ala Val
    370                 375                 380

Lys Tyr Val His Ser Ser Gln His Val Ile Arg Ser Gly Asp Pro Pro
385                 390                 395                 400

Gly Asn Phe Gln Leu Asp Ile Asp Ile Ser Gly Leu Ile Phe Thr His
                405                 410                 415

His Pro Cys Phe Ser Arg Glu His Val Leu Ala Ala Lys Leu Ala Gln
            420                 425                 430

Leu Tyr Asp Gln Tyr Leu Ala Arg His Gln Arg Asn Lys Ala Lys Phe
        435                 440                 445

Leu Thr Asp Lys Leu Gln Ala Leu Arg Asn Ala Val Gln Thr Gly Leu
    450                 455                 460

Asp Pro Glu Lys Pro His Gln Ser Leu Asp Thr Ile Gln Lys Thr Ile
465                 470                 475                 480

Asn Glu Tyr Lys Ser Glu Ile Arg Gln Thr Arg Lys Phe Arg Asp Ala
                485                 490                 495

Glu Gln Glu Lys Asp Arg Thr Leu Leu Lys Thr Ile Ile Lys Val Trp
            500                 505                 510

Lys Glu Met Lys Ser Leu Arg Glu Phe Gln Arg Phe Thr Asn Thr Pro
        515                 520                 525

Leu Lys Leu Val Leu Arg Lys Glu Lys Ala Asp Gln Lys Ala Asp Glu
    530                 535                 540

Glu Ala Tyr Glu Ala Glu Ile Gln Ala Glu Ile Ser Glu Leu Leu Glu
545                 550                 555                 560

Glu His Thr Glu Glu Tyr Ala Gln Lys Met Glu Glu Tyr Arg Thr Ser
                565                 570                 575

Leu Gln Gln Trp Lys Ala Trp Arg Lys Val Gln Arg Ala Lys Lys Lys
            580                 585                 590

Lys Arg Lys Gln Ala Ala Glu Glu His Pro Gly Asp Glu Ile Ala Glu
        595                 600                 605

Pro Tyr Pro Glu Glu Asp Leu Val Lys Pro Ser Pro Pro Glu Pro Thr
    610                 615                 620

Asp Arg Ala Val Ile Glu Gln Glu Val Arg Glu Arg Ala Ala Gln Ser
625                 630                 635                 640
```

```
Arg Arg Arg Pro Trp Glu Pro Thr Leu Val Pro Glu Leu Ser Leu Ala
                645                 650                 655

Gly Ser Val Thr Pro Asn Asp Gln Cys Pro Arg Ala Glu Val Ser Arg
            660                 665                 670

Arg Glu Asp Val Lys Lys Arg Ser Val Tyr Leu Lys Val Leu Phe Asn
        675                 680                 685

Asn Lys Glu Val Ser Arg Thr Val Ser Arg Pro Leu Gly Ala Asp Phe
    690                 695                 700

Arg Val His Phe Gly Gln Ile Phe Asn Leu Gln Ile Val Asn Trp Pro
705                 710                 715                 720

Glu Ser Leu Thr Leu Gln Val Tyr Glu Thr Val Gly His Ser Ser Pro
                725                 730                 735

Thr Leu Leu Ala Glu Val Phe Leu Pro Ile Pro Glu Thr Thr Val Val
            740                 745                 750

Thr Gly Arg Ala Pro Thr Glu Glu Val Glu Phe Ser Ser Asn Gln His
        755                 760                 765

Val Thr Leu Asp His Glu Gly Val Gly Ser Gly Met Glu Ser
    770                 775                 780
```

<210> SEQ ID NO 5
<211> LENGTH: 2424
<212> TYPE: DNA
<213> ORGANISM: Artificial Sequence
<220> FEATURE:
<223> OTHER INFORMATION: representative DNA encoding mutant truncation protein 73-2424

<400> SEQUENCE: 5

```
cttttgtaaa gtttcttaag ctatattcta atggatatgg gctgacatta acaaggaccc     60

atcccagcca aaatgaatcc cagggaagaa aaagtaaaaa taattacaga ggagttcatt    120

gaaaatgatg aggatgcaga catgggaaga cagaataaga actcaaaggt tcgaagacag    180

ccaagaaaga aacagccacc aactgctgtc cccaaggaaa tggtgtccga aaaatcccac    240

cttggcaacc cccaggagcc tgtgcaggag gagcccaaga cccgcctcct gagtatgaca    300

gtccggagag gcccacggag cttacctcca attccttcaa cttccagaac aggctttgca    360

gaattttcca tgaggggacg catgagggag aaattgcaag cagcgaggtc caaagcagaa    420

agtgcattgc tgcaggaaat ccccactcct cggcccagac gcttacgaag tcccagtaag    480

aaagaattgg agactgaatt tggcacagag ccagggaaag aggtagaaag gactcaacaa    540

gaagttgact cccaaagtta ctcaagagtc aagttccatg attctgcacg aaaaatcaag    600

cctaaacccc aggttccacc tggcttccct tctgcagaag aggcctataa cttctttact    660

ttcaactttg atcccgaacc agaaggatca gaggaaaaac caaaagcaag acatagagcg    720

ggaactaatc aagaggagga ggaaggggaa gaagaagaac cacctgcaca aggaggagga    780

aaggaaatgg atgaggaaga actgcttaat ggtgatgatg ccgaggactt cctattgggc    840

ttagatcacg tggctgacga ttttgtagca gtcagacctg cagattatga aagcatccat    900

gatcggctgc agatggaaag agaaatgctc ttcataccca gtaggcagac agtccctaca    960

tataaaaagc ttcctgagaa tgtacagccc aggttcctgg aagatgaagg cctttacacc   1020

ggggtaagac cagaggtggc acgcaccaat cagaacatca tggagaacag attgctgatg   1080

caggaccccg aaagaagatg gtttggagat gacggcagga tcctagctct gccaaacccc   1140

atcaagccat ttccttcaag gccgccagta ctaacacagg agcagagcat taaggcagag   1200

cttgaaacac tgtataaaaa ggctgtaaaa tacgttcaca gtagtcagca tgtgatcaga   1260
```

```
tctggagacc ctcctggaaa tttccaactg gacattgata tttcagggtt aatcttcact   1320

catcatccct gttttagccg agagcatgtt ttggcagcca agctggccca gttatatgac   1380

cagtaccttg caagacacca gagaaacaag gcgaaatttc ttactgataa gctccaagct   1440

ttaagaaatg ctgttcagac tggccttgat ccagaaaaac ctcatcagtc tctcgatacc   1500

atccaaaaaa ccatcaatga gtataaatct gaaattcgac aaacaagaaa attccgtgat   1560

gctgaacaag aaaaagatag aacattgctt aagactatca taaaagtttg gaaagagatg   1620

aaatcccttc gagagttcca gagatttaca aatactccct tgaaacttgt tttgagaaag   1680

gaaaaagctg accagaaagc agatgaagaa gcatatgaag cagaaattca agctgaaata   1740

agtgaactgt tagaagagca cacggaggag tacgcacaga agatggaaga atacagaacg   1800

tcgttacaac agtggaaggc ctggaggaaa gtgcaaaggg ccaagaagaa gaaaaggaaa   1860

caagcagcag aagaacatcc cggtgatgag attgcagagc cgtatcccga ggaggacctt   1920

gtgaagccca gccctccaga gcccactgat cgggcagtga tagagcagga ggtgagggag   1980

agagcagccc agagcaggag gaggccttgg gagcccacgc tggtcccgga gctaagcctg   2040

gcaggaagcg taacacccaa tgaccagtgc cccagagcgg aggtctcgag aagggaggat   2100

gtaaagaagc gctcagtgta cttaaaagtg ctgttcaaca acaaggaggt gtccaggaca   2160

gtcagtcggc cactaggagc agacttccga gttcactttg ggcagatttt caatttgcaa   2220

atagtcaact ggccggagag tttaacactt caggtctatg aaactgtcgg acacagtagt   2280

cccaccttgc tagcagaagt gtttctgcct attcctgaga ctactgttgt cactggaagg   2340

gctcctactg aagaagtgga gtttagcagt aatcagcatg tgacactgga ccacgaggga   2400

gttggaagtg gtatggaaag ctaa                                          2424
```

<210> SEQ ID NO 6
<211> LENGTH: 4890
<212> TYPE: DNA
<213> ORGANISM: Artificial Sequence
<220> FEATURE:
<223> OTHER INFORMATION: representative nucleotide sequence encoding CC2D2A wild-type protein

<400> SEQUENCE: 6

```
cttttgtaaa gtttcttaag ctatattcta atggatatgg gctgacatta acaaggaccc     60

atcccagcca aaatgaatcc cagggaagaa aaagtaaaaa taattacaga ggagttcatt    120

gaaaatgatg aggatgcaga catgggaaga cagaataaga actcaaaggt tcgaagacag    180

ccaagaaaga aacagccacc aactgctgtc cccaaggaaa tggtgtccga aaaatcccac    240

cttggcaacc cccaggagcc tgtgcaggag gagcccaaga cccgcctcct gagtatgaca    300

gtccggagag gcccacggag cttacctcca attccttcaa cttccagaac aggctttgca    360

gaattttcca tgaggggacg catgagggag aaattgcaag cagcgaggtc caaagcagaa    420

agtgcattgc tgcaggaaat ccccactcct cggcccagac gcttacgaag tcccagtaag    480

aaagaattgg agactgaatt tggcacagag ccagggaaag aggtagaaag gactcaacaa    540

gaagttgact cccaaagtta ctcaagagtc aagttccatg attctgcacg aaaaatcaag    600

cctaaacccc aggttccacc tggcttccct tctgcagaag aggcctataa cttctttact    660

ttcaactttg atcccgaacc agaaggatca gaggaaaaac caaaagcaag acatagagcg    720

ggaactaatc aagaggagga ggaaggggaa gaagaagaac cacctgcaca aggaggagga    780

aaggaaatgg atgaggaaga actgcttaat ggtgatgatg ccgaggactt cctattgggc    840

ttagatcacg tggctgacga ttttgtagca gtcagacctg cagattatga aagcatccat    900
```

```
gatcggctgc agatggaaag agaaatgctc ttcataccca gtaggcagac agtccctaca    960
tataaaaagc ttcctgagaa tgtacagccc aggttcctgg aagatgaagg cctttacacc   1020
ggggtaagac cagaggtggc acgcaccaat cagaacatca tggagaacag attgctgatg   1080
caggaccccg aaagaagatg gtttggagat gacggcagga tcctagctct gccaaacccc   1140
atcaagccat ttccttcaag gccgccagta ctaacacagg agcagagcat taaggcagag   1200
cttgaaacac tgtataaaaa ggctgtaaaa tacgttcaca gtagtcagca tgtgatcaga   1260
tctggagacc ctcctggaaa tttccaactg gacattgata tttcagggtt aatcttcact   1320
catcatccct gttttagccg agagcatgtt ttggcagcca agctggccca gttatatgac   1380
cagtaccttg caagacacca gagaaacaag gcgaaatttc ttactgataa gctccaagct   1440
ttaagaaatg ctgttcagac tggccttgat ccagaaaaac ctcatcagtc tctcgatacc   1500
atccaaaaaa ccatcaatga gtataaatct gaaattcgac aaacaagaaa attccgtgat   1560
gctgaacaag aaaaagatag aacattgctt aagactatca taaaagtttg gaaagagatg   1620
aaatcccttc gagagttcca gagatttaca aatactccct tgaaacttgt tttgagaaag   1680
gaaaaagctg accagaaagc agatgaagaa gcatatgaag cagaaattca agctgaaata   1740
agtgaactgt tagaagagca cacggaggag tacgcacaga agatggaaga atacagaacg   1800
tcgttacaac agtggaaggc ctggaggaaa gtgcaaaggg ccaagaagaa gaaaaggaaa   1860
caagcagcag aagaacatcc cggtgatgag attgcagagc cgtatcccga ggaggacctt   1920
gtgaagccca gccctccaga gcccactgat cgggcagtga tagagcagga ggtgagggag   1980
agagcagccc agagcaggag gaggccttgg gagcccacgc tggtcccgga gctaagcctg   2040
gcaggaagcg taacacccaa tgaccagtgc cccagagcgg aggtctcgag aagggaggat   2100
gtaaagaagc gctcagtgta cttaaaagtg ctgttcaaca acaaggaggt gtccaggaca   2160
gtcagtcggc cactaggagc agacttccga gttcactttg ggcagatttt caatttgcaa   2220
atagtcaact ggccggagag tttaacactt caggtctatg aaactgtcgg acacagtagt   2280
cccaccttgc tagcagaagt gtttctgcct attcctgaga ctactgttgt cactggaagg   2340
gctcctactg aagaagtgga gtttagcagt aatcagcatg tgacactgga ccacgaggga   2400
gttggaagtg gagtgccctt ctcatttgaa gctgatggca gtaaccagct gactctgatg   2460
acctcaggga aagtgtctca tagtgtggca tgggccattg gagaaaacgg gatacccttta   2520
attcctccat tgtcacagca gaacatcgga tttcggagtg ctttgaagaa agcagatgcc   2580
atctcatcta ttggcacatc aggactgaca gacatgaaaa aattggccaa gtgggcagca   2640
gagtccaagc tcgacccaaa tgaccccaac aatgcccctt tgatgcagct tatctcggtt   2700
gctaccagtg gtgaatccta tgtccctgat ttctttagac tggagcagct gcaacaggag   2760
tttaactttg tttcagatca agaattaaat agatccaaac gatttaggct tcttcatctt   2820
agaagccaag aggtgccaga attccgaaat tataagcaag ttccagtcta tgaccgagaa   2880
attatggaaa aggtattcca ggactatgag aaacggttac gagacagaaa tgtaatagaa   2940
accaaggaac acatagacac ccatagggcc atagtagcca agtacctcca gcaggttaga   3000
gaatcagtga taaatcgttt cttaattgca aaacaatatt ttcttcttgc tgatatgata   3060
gtagaagaag aagttcccaa tatcagcatt ttgggcctaa gccttttcaa gctggcagaa   3120
caaaagcgac cactgcggcc aaggagaaaa ggtcggaaga aggtgacagc ccaaaacctg   3180
tctgatggag acataaagct gctggtgaac attgtgcgag cttacgacat tccagtgagg   3240
aagccggcag tgagcaaatt ccagcagccg tcgaggtctt caaggatgtt cagtgaaaag   3300
```

```
catgctgctt ccccaagcac gtacagccca acccacaatg ctgactaccc cctcggccag   3360

gttttagtac gtccctttgt agaagtctct tttcaacgaa cagtttgcca tacgactacg   3420

gctgaaggac caaaccctag ctggaatgaa gaactagaac ttccatttag ggctcctaat   3480

ggagattata gcacagccag tctgcagtca gtgaaagatg ttgtgttcat taacattttt   3540

gatgaagtac tgcatgatgt cttagaggat gaccgtgaaa gaggaagtgg aatccatact   3600

cgtattgaga gacactggct gggatgtgtg aaaatgccat ttagcacaat atatttccaa   3660

gcaaggtttg agtctcagga agatgagaaa ttacttcaag caactgagaa gtttcaagct   3720

gaatgtgcct taaagtttcc aaatcgtcag tgccttacaa cagtaattga tataagcgga   3780

aaaactgttt ttatcacacg ttatctcaaa cctttaaacc ctcctcagga gctccttaat   3840

gtctacccca ataatctaca ggcaactgca gaactggtgg ctcgatatgt gtccttgatt   3900

cccttcttgc ctgacactgt ctcatttggt ggtatctgtg acctctggag cacatctgat   3960

caatttcttg atctcctggc aggggatgaa gaagaacatg cagtactatt gtgtaattac   4020

tttctgtctc tgggtaagaa ggcctggctg ttgatgggca atgctattcc tgagggtcca   4080

actgcctatg tgctaacttg ggagcaaggt cgttatttaa tatggaatcc ctgcagtgga   4140

catttttatg gacaatttga tacattctgt cccttgaaaa atgtgggctg tttaataggt   4200

cctgacaata tttggtttaa tattcaacga tatgaatctc cactaaggat aaattttgat   4260

gtcaccaggc ccaagctatg gaaatctttc ttttcaagaa gccttccata tcctggcctt   4320

tccagtgttc agcctgaaga gctaatttac cagcgctcag acaaagcagc tgcagctgag   4380

ctacaagaca ggattgaaaa aatactaaaa gaaaaaatca tggactggag gccacgccat   4440

ctgactcggt ggaataggta ttgtacctct actctgcgtc acttcttgcc tctgttagaa   4500

aaaagtcaag gagaagatgt agaagatgac cacagagcag aactgctaaa acagctggga   4560

gactacaggt tctctggatt tcctcttcac atgccttatt ctgaagtgaa gcctttaatt   4620

gacgctgtgt atagtactgg agtacataat attgatgttc ctaatgttga atttgcttta   4680

gctgtataca tacacccata ccccaaaaat gttttgtctg tttggatcta tgttgcctct   4740

cttatacgca acaggtaatt tttttcactg tactttctgt atcatgtaaa aactacactt   4800

aggatatgag aaaattttaa attatatgca tcacatcaga agaacatatt attggcaaat   4860

aataaaatta tcaactgttt tcaaactgtg                                    4890
```

```
<210> SEQ ID NO 7
<211> LENGTH: 1561
<212> TYPE: PRT
<213> ORGANISM: Artificial Sequence
<220> FEATURE:
<223> OTHER INFORMATION: representative amino acid sequence of wild type
      CC2D2A protein

<400> SEQUENCE: 7

Met Asn Pro Arg Glu Glu Lys Val Lys Ile Ile Thr Glu Glu Phe Ile
1               5                   10                  15

Glu Asn Asp Glu Asp Ala Asp Met Gly Arg Gln Asn Lys Asn Ser Lys
            20                  25                  30

Val Arg Arg Gln Pro Arg Lys Lys Gln Pro Pro Thr Ala Val Pro Lys
        35                  40                  45

Glu Met Val Ser Glu Lys Ser His Leu Gly Asn Pro Gln Glu Pro Val
    50                  55                  60

Gln Glu Glu Pro Lys Thr Arg Leu Leu Ser Met Thr Val Arg Arg Gly
65                  70                  75                  80
```

-continued

```
Pro Arg Ser Leu Pro Pro Ile Pro Ser Thr Ser Arg Thr Gly Phe Ala
                85                  90                  95

Glu Phe Ser Met Arg Gly Arg Met Arg Glu Lys Leu Gln Ala Ala Arg
            100                 105                 110

Ser Lys Ala Glu Ser Ala Leu Leu Gln Glu Ile Pro Thr Pro Arg Pro
        115                 120                 125

Arg Arg Leu Arg Ser Pro Ser Lys Lys Glu Leu Glu Thr Glu Phe Gly
    130                 135                 140

Thr Glu Pro Gly Lys Glu Val Glu Arg Thr Gln Gln Glu Val Asp Ser
145                 150                 155                 160

Gln Ser Tyr Ser Arg Val Lys Phe His Asp Ser Ala Arg Lys Ile Lys
                165                 170                 175

Pro Lys Pro Gln Val Pro Pro Gly Phe Pro Ser Ala Glu Glu Ala Tyr
            180                 185                 190

Asn Phe Phe Thr Phe Asn Phe Asp Pro Glu Pro Glu Gly Ser Glu Glu
        195                 200                 205

Lys Pro Lys Ala Arg His Arg Ala Gly Thr Asn Gln Glu Glu Glu Glu
    210                 215                 220

Gly Glu Glu Glu Glu Pro Pro Ala Gln Gly Gly Gly Lys Glu Met Asp
225                 230                 235                 240

Glu Glu Glu Leu Leu Asn Gly Asp Asp Ala Glu Asp Phe Leu Leu Gly
                245                 250                 255

Leu Asp His Val Ala Asp Asp Phe Val Ala Val Arg Pro Ala Asp Tyr
            260                 265                 270

Glu Ser Ile His Asp Arg Leu Gln Met Glu Arg Glu Met Leu Phe Ile
        275                 280                 285

Pro Ser Arg Gln Thr Val Pro Thr Tyr Lys Lys Leu Pro Glu Asn Val
    290                 295                 300

Gln Pro Arg Phe Leu Glu Asp Glu Gly Leu Tyr Thr Gly Val Arg Pro
305                 310                 315                 320

Glu Val Ala Arg Thr Asn Gln Asn Ile Met Glu Asn Arg Leu Leu Met
                325                 330                 335

Gln Asp Pro Glu Arg Arg Trp Phe Gly Asp Asp Gly Arg Ile Leu Ala
            340                 345                 350

Leu Pro Asn Pro Ile Lys Pro Phe Pro Ser Arg Pro Pro Val Leu Thr
        355                 360                 365

Gln Glu Gln Ser Ile Lys Ala Glu Leu Glu Thr Leu Tyr Lys Lys Ala
    370                 375                 380

Val Lys Tyr Val His Ser Ser Gln His Val Ile Arg Ser Gly Asp Pro
385                 390                 395                 400

Pro Gly Asn Phe Gln Leu Asp Ile Asp Ile Ser Gly Leu Ile Phe Thr
                405                 410                 415

His His Pro Cys Phe Ser Arg Glu His Val Leu Ala Ala Lys Leu Ala
            420                 425                 430

Gln Leu Tyr Asp Gln Tyr Leu Ala Arg His Gln Arg Asn Lys Ala Lys
        435                 440                 445

Phe Leu Thr Asp Lys Leu Gln Ala Leu Arg Asn Ala Val Gln Thr Gly
    450                 455                 460

Leu Asp Pro Glu Lys Pro His Gln Ser Leu Asp Thr Ile Gln Lys Thr
465                 470                 475                 480

Ile Asn Glu Tyr Lys Ser Glu Ile Arg Gln Thr Arg Lys Phe Arg Asp
                485                 490                 495

Ala Glu Gln Glu Lys Asp Arg Thr Leu Leu Lys Thr Ile Ile Lys Val
```

```
            500                 505                 510

Trp Lys Glu Met Lys Ser Leu Arg Glu Phe Gln Arg Phe Thr Asn Thr
        515                 520                 525

Pro Leu Lys Leu Val Leu Arg Lys Glu Lys Ala Asp Gln Lys Ala Asp
    530                 535                 540

Glu Glu Ala Tyr Glu Ala Glu Ile Gln Ala Glu Ile Ser Glu Leu Leu
545                 550                 555                 560

Glu Glu His Thr Glu Glu Tyr Ala Gln Lys Met Glu Glu Tyr Arg Thr
                565                 570                 575

Ser Leu Gln Gln Trp Lys Ala Trp Arg Lys Val Gln Arg Ala Lys Lys
            580                 585                 590

Lys Lys Arg Lys Gln Ala Ala Glu Glu His Pro Gly Asp Glu Ile Ala
        595                 600                 605

Glu Pro Tyr Pro Glu Glu Asp Leu Val Lys Pro Ser Pro Pro Glu Pro
    610                 615                 620

Thr Asp Arg Ala Val Ile Glu Gln Glu Val Arg Glu Arg Ala Ala Gln
625                 630                 635                 640

Ser Arg Arg Arg Pro Trp Glu Pro Thr Leu Val Pro Glu Leu Ser Leu
                645                 650                 655

Ala Gly Ser Val Thr Pro Asn Asp Gln Cys Pro Arg Ala Glu Val Ser
            660                 665                 670

Arg Arg Glu Asp Val Lys Lys Arg Ser Val Tyr Leu Lys Val Leu Phe
        675                 680                 685

Asn Asn Lys Glu Val Ser Arg Thr Val Ser Arg Pro Leu Gly Ala Asp
    690                 695                 700

Phe Arg Val His Phe Gly Gln Ile Phe Asn Leu Gln Ile Val Asn Trp
705                 710                 715                 720

Pro Glu Ser Leu Thr Leu Gln Val Tyr Glu Thr Val Gly His Ser Ser
                725                 730                 735

Pro Thr Leu Leu Ala Glu Val Phe Leu Pro Ile Pro Glu Thr Thr Val
            740                 745                 750

Val Thr Gly Arg Ala Pro Thr Glu Glu Val Glu Phe Ser Ser Asn Gln
        755                 760                 765

His Val Thr Leu Asp His Glu Gly Val Gly Ser Gly Val Pro Phe Ser
    770                 775                 780

Phe Glu Ala Asp Gly Ser Asn Gln Leu Thr Leu Met Thr Ser Gly Lys
785                 790                 795                 800

Val Ser His Ser Val Ala Trp Ala Ile Gly Glu Asn Gly Ile Pro Leu
                805                 810                 815

Ile Pro Pro Leu Ser Gln Gln Asn Ile Gly Phe Arg Ser Ala Leu Lys
            820                 825                 830

Lys Ala Asp Ala Ile Ser Ser Ile Gly Thr Ser Gly Leu Thr Asp Met
        835                 840                 845

Lys Lys Leu Ala Lys Trp Ala Ala Glu Ser Lys Leu Asp Pro Asn Asp
    850                 855                 860

Pro Asn Asn Ala Pro Leu Met Gln Leu Ile Ser Val Ala Thr Ser Gly
865                 870                 875                 880

Glu Ser Tyr Val Pro Asp Phe Phe Arg Leu Glu Gln Leu Gln Gln Glu
                885                 890                 895

Phe Asn Phe Val Ser Asp Gln Glu Leu Asn Arg Ser Lys Arg Phe Arg
            900                 905                 910

Leu Leu His Leu Arg Ser Gln Glu Val Pro Glu Phe Arg Asn Tyr Lys
        915                 920                 925
```

```
Gln Val Pro Val Tyr Asp Arg Glu Ile Met Glu Lys Val Phe Gln Asp
    930                 935                 940

Tyr Glu Lys Arg Leu Arg Asp Arg Asn Val Ile Glu Thr Lys Glu His
945                 950                 955                 960

Ile Asp Thr His Arg Ala Ile Val Ala Lys Tyr Leu Gln Gln Val Arg
                965                 970                 975

Glu Ser Val Ile Asn Arg Phe Leu Ile Ala Lys Gln Tyr Phe Leu Leu
            980                 985                 990

Ala Asp Met Ile Val Glu Glu Glu  Val Pro Asn Ile Ser  Ile Leu Gly
        995                 1000                 1005

Leu Ser  Leu Phe Lys Leu Ala  Glu Gln Lys Arg Pro  Leu Arg Pro
    1010                 1015                 1020

Arg Arg  Lys Gly Arg Lys Lys  Val Thr Ala Gln Asn  Leu Ser Asp
    1025                 1030                 1035

Gly Asp  Ile Lys Leu Leu Val  Asn Ile Val Arg Ala  Tyr Asp Ile
    1040                 1045                 1050

Pro Val  Arg Lys Pro Ala Val  Ser Lys Phe Gln Gln  Pro Ser Arg
    1055                 1060                 1065

Ser Ser  Arg Met Phe Ser Glu  Lys His Ala Ala Ser  Pro Ser Thr
    1070                 1075                 1080

Tyr Ser  Pro Thr His Asn Ala  Asp Tyr Pro Leu Gly  Gln Val Leu
    1085                 1090                 1095

Val Arg  Pro Phe Val Glu Val  Ser Phe Gln Arg Thr  Val Cys His
    1100                 1105                 1110

Thr Thr  Thr Ala Glu Gly Pro  Asn Pro Ser Trp Asn  Glu Glu Leu
    1115                 1120                 1125

Glu Leu  Pro Phe Arg Ala Pro  Asn Gly Asp Tyr Ser  Thr Ala Ser
    1130                 1135                 1140

Leu Gln  Ser Val Lys Asp Val  Val Phe Ile Asn Ile  Phe Asp Glu
    1145                 1150                 1155

Val Leu  His Asp Val Leu Glu  Asp Asp Arg Glu Arg  Gly Ser Gly
    1160                 1165                 1170

Ile His  Thr Arg Ile Glu Arg  His Trp Leu Gly Cys  Val Lys Met
    1175                 1180                 1185

Pro Phe  Ser Thr Ile Tyr Phe  Gln Ala Arg Phe Glu  Ser Gln Glu
    1190                 1195                 1200

Asp Glu  Lys Leu Leu Gln Ala  Thr Glu Lys Phe Gln  Ala Glu Cys
    1205                 1210                 1215

Ala Leu  Lys Phe Pro Asn Arg  Gln Cys Leu Thr Thr  Val Ile Asp
    1220                 1225                 1230

Ile Ser  Gly Lys Thr Val Phe  Ile Thr Arg Tyr Leu  Lys Pro Leu
    1235                 1240                 1245

Asn Pro  Pro Gln Glu Leu Leu  Asn Val Tyr Pro Asn  Asn Leu Gln
    1250                 1255                 1260

Ala Thr  Ala Glu Leu Val Ala  Arg Tyr Val Ser Leu  Ile Pro Phe
    1265                 1270                 1275

Leu Pro  Asp Thr Val Ser Phe  Gly Gly Ile Cys Asp  Leu Trp Ser
    1280                 1285                 1290

Thr Ser  Asp Gln Phe Leu Asp  Leu Leu Ala Gly Asp  Glu Glu Glu
    1295                 1300                 1305

His Ala  Val Leu Leu Cys Asn  Tyr Phe Leu Ser Leu  Gly Lys Lys
    1310                 1315                 1320

Ala Trp  Leu Leu Met Gly Asn  Ala Ile Pro Glu Gly  Pro Thr Ala
    1325                 1330                 1335
```

```
Tyr Val  Leu Thr Trp Glu Gln  Gly Arg Tyr Leu Ile  Trp Asn Pro
    1340                 1345                 1350

Cys Ser  Gly His Phe Tyr Gly  Gln Phe Asp Thr Phe  Cys Pro Leu
    1355                 1360                 1365

Lys Asn  Val Gly Cys Leu Ile  Gly Pro Asp Asn Ile  Trp Phe Asn
    1370                 1375                 1380

Ile Gln  Arg Tyr Glu Ser Pro  Leu Arg Ile Asn Phe  Asp Val Thr
    1385                 1390                 1395

Arg Pro  Lys Leu Trp Lys Ser  Phe Phe Ser Arg Ser  Leu Pro Tyr
    1400                 1405                 1410

Pro Gly  Leu Ser Ser Val Gln  Pro Glu Glu Leu Ile  Tyr Gln Arg
    1415                 1420                 1425

Ser Asp  Lys Ala Ala Ala Ala  Glu Leu Gln Asp Arg  Ile Glu Lys
    1430                 1435                 1440

Ile Leu  Lys Glu Lys Ile Met  Asp Trp Arg Pro Arg  His Leu Thr
    1445                 1450                 1455

Arg Trp  Asn Arg Tyr Cys Thr  Ser Thr Leu Arg His  Phe Leu Pro
    1460                 1465                 1470

Leu Leu  Glu Lys Ser Gln Gly  Glu Asp Val Glu Asp  Asp His Arg
    1475                 1480                 1485

Ala Glu  Leu Leu Lys Gln Leu  Gly Asp Tyr Arg Phe  Ser Gly Phe
    1490                 1495                 1500

Pro Leu  His Met Pro Tyr Ser  Glu Val Lys Pro Leu  Ile Asp Ala
    1505                 1510                 1515

Val Tyr  Ser Thr Gly Val His  Asn Ile Asp Val Pro  Asn Val Glu
    1520                 1525                 1530

Phe Ala  Leu Ala Val Tyr Ile  His Pro Tyr Pro Lys  Asn Val Leu
    1535                 1540                 1545

Ser Val  Trp Ile Tyr Val Ala  Ser Leu Ile Arg Asn  Arg
    1550                 1555                 1560
```

<210> SEQ ID NO 8
<211> LENGTH: 20
<212> TYPE: DNA
<213> ORGANISM: Artificial Sequence
<220> FEATURE:
<223> OTHER INFORMATION: forward primer from exon 18

<400> SEQUENCE: 8
acagtcagtc ggccactagg 20

<210> SEQ ID NO 9
<211> LENGTH: 20
<212> TYPE: DNA
<213> ORGANISM: Artificial Sequence
<220> FEATURE:
<223> OTHER INFORMATION: reverse primer from exon 25

<400> SEQUENCE: 9
gttctgccag cttgaaaagg 20

<210> SEQ ID NO 10
<211> LENGTH: 22
<212> TYPE: PRT
<213> ORGANISM: Artificial Sequence
<220> FEATURE:
<223> OTHER INFORMATION: first epitope from CC2D2A protein

<400> SEQUENCE: 10

```
Arg Ser Lys Arg Phe Arg Leu Leu His Leu Arg Ser Gln Glu Val Pro
1               5                   10                  15

Glu Phe Arg Asn Tyr Lys
            20


<210> SEQ ID NO 11
<211> LENGTH: 22
<212> TYPE: PRT
<213> ORGANISM: Artificial Sequence
<220> FEATURE:
<223> OTHER INFORMATION: second epitope from CC2D2A protein

<400> SEQUENCE: 11

Glu Asp Asp His Arg Ala Glu Leu Leu Lys Gln Leu Gly Asp Tyr Arg
1               5                   10                  15

Phe Ser Gly Phe Pro Leu
            20


<210> SEQ ID NO 12
<211> LENGTH: 9
<212> TYPE: PRT
<213> ORGANISM: Artificial Sequence
<220> FEATURE:
<223> OTHER INFORMATION: putative nuclear localization signal

<400> SEQUENCE: 12

Gln Arg Ala Lys Lys Lys Lys Arg Lys
1               5


<210> SEQ ID NO 13
<211> LENGTH: 5
<212> TYPE: PRT
<213> ORGANISM: Artificial Sequence
<220> FEATURE:
<223> OTHER INFORMATION: putative nuclear localization signal

<400> SEQUENCE: 13

Arg Pro Arg Arg Lys
1               5
```

CC2D2A GENE MUTATIONS ASSOCIATED WITH JOUBERT SYNDROME AND DIAGNOSTIC METHODS FOR IDENTIFYING THE SAME

This application is a 371 filing of International Patent Application PCT/CA2008/001760 filed Oct. 3, 2008, which claims the benefit of application No. 60/977,803 filed Oct. 5, 2007.

FIELD OF INVENTION

The present invention relates to gene mutations. More specifically, the present invention relates to gene mutations associated with mental retardation.

BACKGROUND OF THE INVENTION

Mental retardation (MR) is a condition that affects about 6 million American and over half a million Canadian children under the age of 14 years (Shea, 2006). MR is a general term for a heterogeneous group of disorders that are defined by deficits in cognitive and adaptive development. Frequently other terms used include “general learning disorder”, “mental handicap”, “learning disability”, “intellectual handicap”, and “intellectual disability” (Leonard & Wen, 2002), also “mentally challenged” and “developmental delay” (Shea, 2006). The prevalence of MR is commonly given as about 1% of the population (Szymanski & King, 1999), with a higher proportion of males to females affected (1.4:1; Murphy et al, 1998).

MR is commonly classified according to Intelligent Quotient (IQ). The Diagnostic & Statistical Manual of Mental Disorders (4th Edition; DSM-IV, 1994) identifies mild MR in the IQ range 50-55 to 70, moderate MR as 35-40 to 50-55, severe MR as 20-25 to 35-40, and profound MR as below 20-25. Attempts to understand the etiological basis of cases of MR are important because they may assist with the diagnosis of associated co-morbidities (e.g. aortic stenosis in Williams syndrome), or may help with prenatal diagnostics and/or genetic counselling (e.g. in fragile X syndrome), or may identify a treatable condition such as phenylketonuria (Shea, 2006). In addition, understanding the cause of MR may help families cope with a MR child and may help them access support infrastructure.

The contribution of genetics to MR has long been established. Conventionally, genetic forms of MR are subdivided into two major categories. Firstly, syndromic MR is characterized by cognitive deficits associated with other clinical and biological features. Secondly, non-syndromic form of MR in which cognitive impairment is the only manifestation of disease. Genetic factors are involved in the etiology of approximately two-thirds of mental retardation cases (Curry, 2002). In inherited forms of mental retardation, X-linkage or autosomal recessive inheritance patterns are the most plausible, since procreation from affected individuals is not common. To-date, more than 60 genes have been reported for X linked mental retardation (Chelly et al, 2006). But the molecular basis of autosomal recessive mental retardations are still poorly understood. Although autosomal recessive inheritance is estimated to be involved in nearly a quarter of all individuals with non-syndromic mental retardation (NSMR)(reviewed in Basel-Vanagaite et al,[7]), only four autosomal genes, the PRSS12 gene on chromosome 4q26 (neurotrypsin [MIM #606709]), the CC2D1A gene on chromosome 19p13.12 [MIM #610055], the CRBN gene on chromosome 3p26 (cereblon [MIM #609262]), and very recently GRIK2 on 6q16.1-q21 (ionotropic glutamate receptor 6 [MIM #138244]) have been reported so far to cause autosomal recessive NSMR.[7-10] However, only a very few families or unrelated individuals with ARMR have been confirmed for each of these genes (PRSS12, N=1; CRBN, N=1; CC2D1A, N=9; GRIK2, N=1). The most recent of these genes, GRIK2, was discovered at one of 8 novel loci for autosomal recessive non-syndromic mental retardation (NSMR) recently mapped by homozygosity mapping in 78 consanguineous Iranian families. However, no disease gene or mutation has yet been reported for the other 7 loci (Najmabadi et al, 2007). Neurotrypsin (PRSS12) was the first gene reported in etiology of autosomal recessive non-syndromic mental retardation. The disease locus was mapped on chromosome 4q24-q25 by homozygosity mapping using a set 400 microsatellite markers across the genome. This interval encompasses about 29 genes of known function including the DKK2, PL34, CASP6, ANK2, CAMK2D TRPC3, and PRSS12 genes. A homozygous 4 by deletion in exon 7 of the PRSS12 gene was found cosegregating in all affected individuals, and resulted in a premature stop codon, 147 by downstream of the deletion (Molinari et al, 2002). In another family with mild autosomal recessive non-syndromic mental retardation, a nonsense mutation causing a premature stop codon was identified in the CRBN gene that encodes for an ATP-dependent Lon protease. This C to T substitution changed an arginine residue to a stop codon in exon 11 (R419X) of this gene (Higgins et al, 2004). Mutations in the PRSS12 and CRBN genes have each been reported in only one family to-date. Recently a protein truncating mutation was identified in the CC2D1A gene in nine consanguineous families with severe autosomal recessive NSMR. The CC2D1A protein is involved in the calcium dependent phospholipid binding (Basel-Vanagaite et al, 2006).

A recent study has mapped 8 novel loci for autosomal recessive non-syndromic mental retardation (NSMR) by homozygosity mapping in 78 consanguineous Iranian families. However, no disease gene or mutation has yet been reported (Najmabadi et al, 2007). Another recently published study has mapped a new locus for autosomal recessive non-syndromic mental retardation to 1p21.1-p13.3 (Uyguner, 2007).

There is a need in the art to identify genetic markers associated with mental retardation. Further there is a need in the art to identify nucleotide sequences associated with mental retardation. There is also a need in the art for new diagnostic assays for mental retardation.

SUMMARY OF THE INVENTION

The present invention relates to gene mutations. More specifically, the present invention relates to gene mutations associated with mental retardation.

According to the present invention there is provided a protein comprising a fragment of SEQ ID NO:7. In a preferred embodiment the protein is truncated at amino acid 779 or earlier. In an alternate embodiment, the protein has all or part of the C2 domain abolished. Other proteins are also contemplated as described herein.

According to the present invention there is provided a protein comprising an amino acid sequence that terminates in DHEGGSGMES (SEQ ID NO:1).

According to the present invention, there is also provided the protein as defined above, wherein the amino acid sequence comprises SEQ ID NO:2, SEQ ID NO:3 or SEQ ID NO:4.

Also provided by the present invention is the protein as described above wherein the protein is between about 80% and 100% identical to SEQ ID NO:3.

The present invention also provides a nucleic acid encoding the protein as defined above.

Also provided by the present invention is the nucleic acid as defined above encoding the protein defined by SEQ ID NO:3 or 4.

The present invention also provides a nucleic acid comprising the complement of the nucleic acid defined above. In still a further non-limiting embodiment, the nucleic acid is capable of hybridizing to the nucleic acid defined above or its complement under stringent hybridization conditions.

The present invention also provides a nucleic acid as defined above comprising between 7 and 100 nucleotides. Further, the nucleic acid may be labeled at one or more sites.

Also provided by the present invention is a nucleotide sequence as defined above wherein the sequence is in a nucleotide construct comprising one or more regulatory elements.

The present invention also provides a method of screening a subject for a gene sequence associated with mental retardation comprising, a) obtaining a biological sample from the subject, the biological sample comprising DNA or RNA, and;

b) assaying the sample for a nucleic acid encoding a protein comprising SEQ ID NO:1 at the C-terminus, wherein the presence of the nucleic acid indicates that the subject has a gene sequence associated with mental retardation.

In such a method, the step of assaying may comprise one or more hybridization assays, nucleotide sequencing, polymerase chain reactions (PCR) or any combination thereof.

The present invention also provides a method of screening as defined above wherein the sample that is assayed is a blood sample.

The present invention further provides a method of screening a subject for mutant protein associated with mental retardation, the method comprising, a) obtaining a biological sample from the subject, b) testing the sample for a protein that comprises SEQ ID NO:1 at the C-terminus thereof, wherein the presence of the protein indicates that the subject has a gene sequence that expresses a mutant protein associated with mental retardation.

The present invention also provides a method of screening a subject for mutant protein associated with mental retardation, the method comprising, a) obtaining a biological sample from the subject, b) testing the sample for a protein that comprises SEQ ID NO:1 at the C-terminus thereof, wherein the presence of the protein indicates that the subject has a gene sequence that expresses a mutant protein associated with mental retardation.

The present invention also provides a method of screening a subject for a gene sequence associated with mental retardation, the method comprising, a) obtaining a biological sample from the subject, the biological sample comprising DNA or RNA, and;

b) assaying the sample for one or more mutations in a nucleotide sequence encoding a CC2D2A protein as defined by SEQ ID NO:7, an isoform or a naturally occurring allelic variant thereof, wherein the presence of said one or more mutations results in deletion in one or more amino acids of the protein or premature truncation of the protein and indicates that the subject has a gene sequence associated with mental retardation.

Also provided by the present invention is a method as defined above, wherein the one or more mutations are deletions, inversions, translocations, duplications, splice-donor site mutations, point-mutations or the like.

Also provided by the present invention is a method as defined above, wherein the one or more mutations occur in exon 19.

Also provided by the present invention is a method as defined above, wherein the one or more mutations abolish all or part of the C2 domain.

Also provided by the present invention is a method as defined above, wherein the one or more mutations result in truncation of the CC2D2A protein at amino acid 779 or earlier.

Also provided by the present invention is a method as defined above, wherein the one or more mutations add one or more nonsense amino acids to the protein.

The present invention also contemplates a kit comprising, a) a protein comprising an amino acid sequence that terminates in DHEGGSGMES (SEQ ID NO:1) and that is associated with mental retardation, b) a truncated version of the protein defined by SEQ ID NO:7 or a protein wherein all or part of the C2 domain is deleted;

c) an antibody that selectively binds to the protein in a), b) or a) and b) but preferably not a similar CC2D2A wild-type protein that is not associated with mental retardation, d) one or more nucleic acid primers to amplify a nucleotide sequence encoding a protein or fragment thereof which comprises a mutation associated with mental retardation as provided herein, e) one or more nucleic acid probes of between about 9 and 100 nucleotides that hybridize to the nucleotide sequence encoding a protein or fragment thereof which comprises a mutation associated mental retardation as provided herein, f) one or more reagents comprising buffer(s), dATP, dTTP, dCTP, dGTP, DNA polymerase(s), or a combination thereof;

g) instructions for assaying, diagnosing or determining the presence of a nucleotide sequence or protein that is associated with mental retardation in a subject, h) instructions for using any component or practicing any method as described herein, or; any combination or subcombination thereof.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows representative protein and nucleotide sequences as defined herein including a) a first CC2D2A truncation protein associated with mental retardation plus retinitis pigmentosa, b) a second CC2D2A truncation protein associated with mental retardation plus retinitis pigmentosa, c) a representative nucleotide sequence encoding a CC2D2A truncation protein, d) a representative wild-type CC2D2A nucleotide sequence encoding a non-truncated protein, and e) a representative wild-type CC2D2A protein.

DETAILED DESCRIPTION

Figure 2:
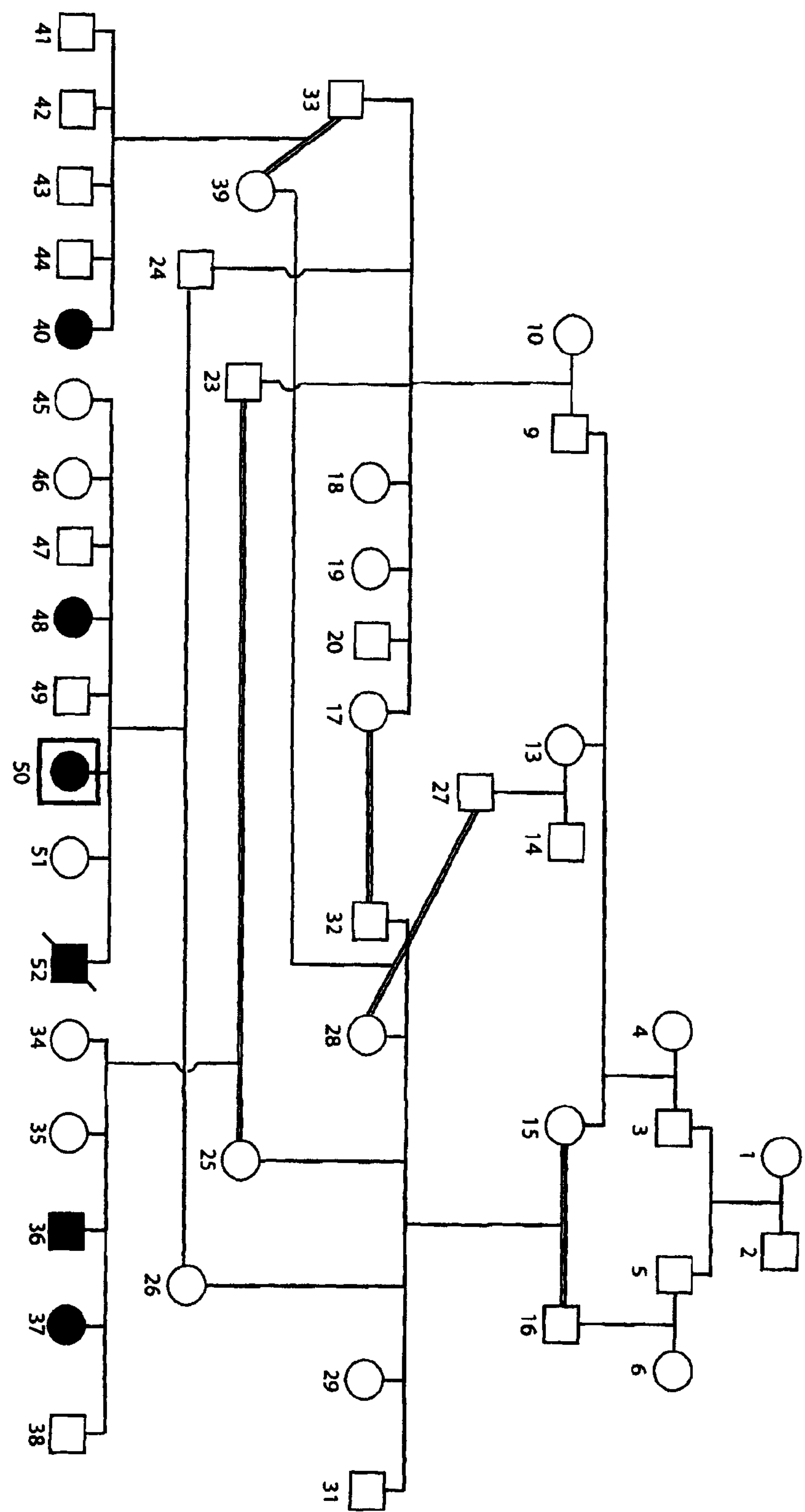
FIG. 2 shows a graphic depiction of the pedigree of the family from the Mianwali district.
Figure 3A:
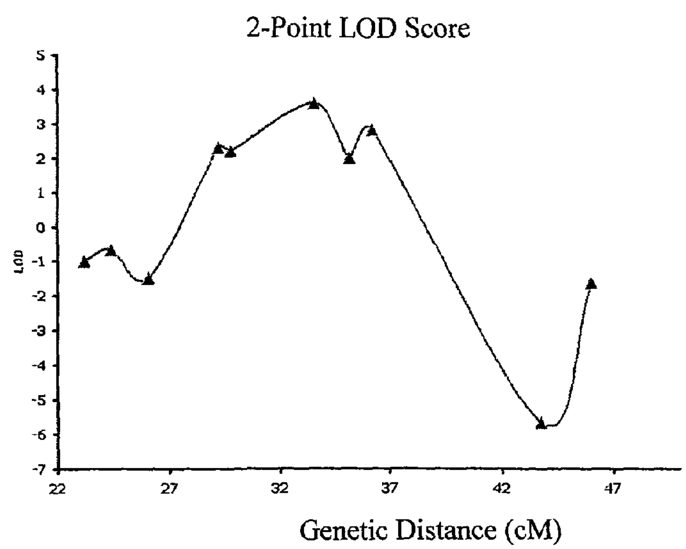
FIG. 3 shows a graphical depiction of the two-point and multi-point linkage analysis for the Mianwali family.
Figure 3B:
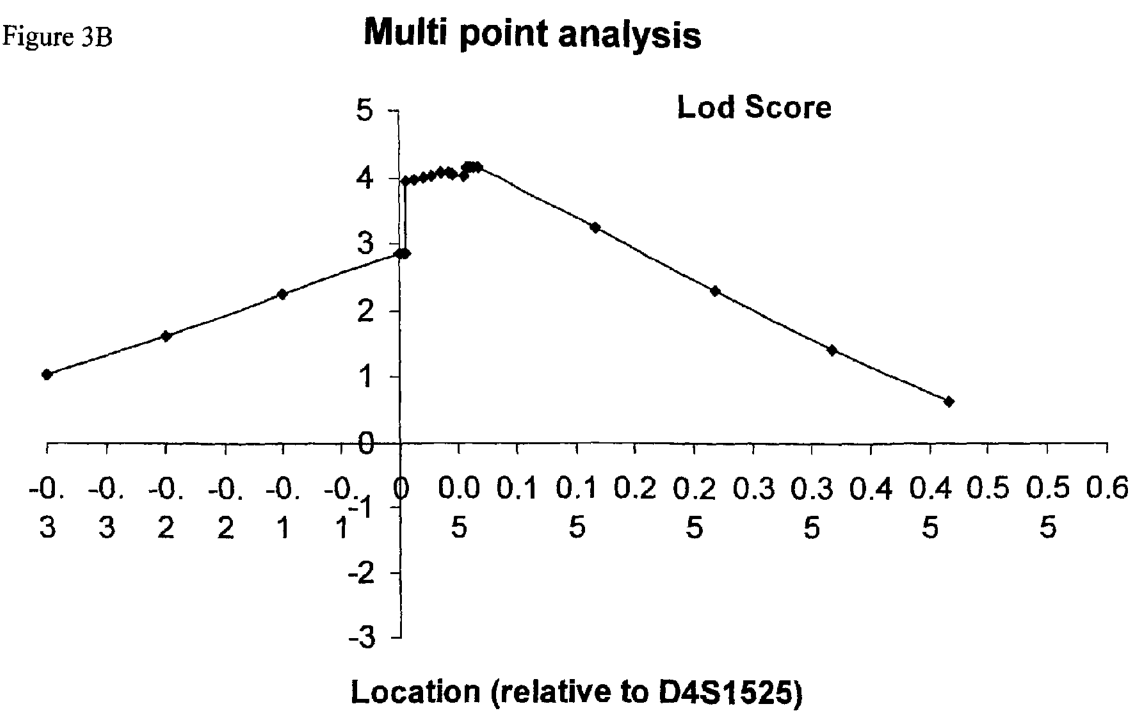
Figure 4:
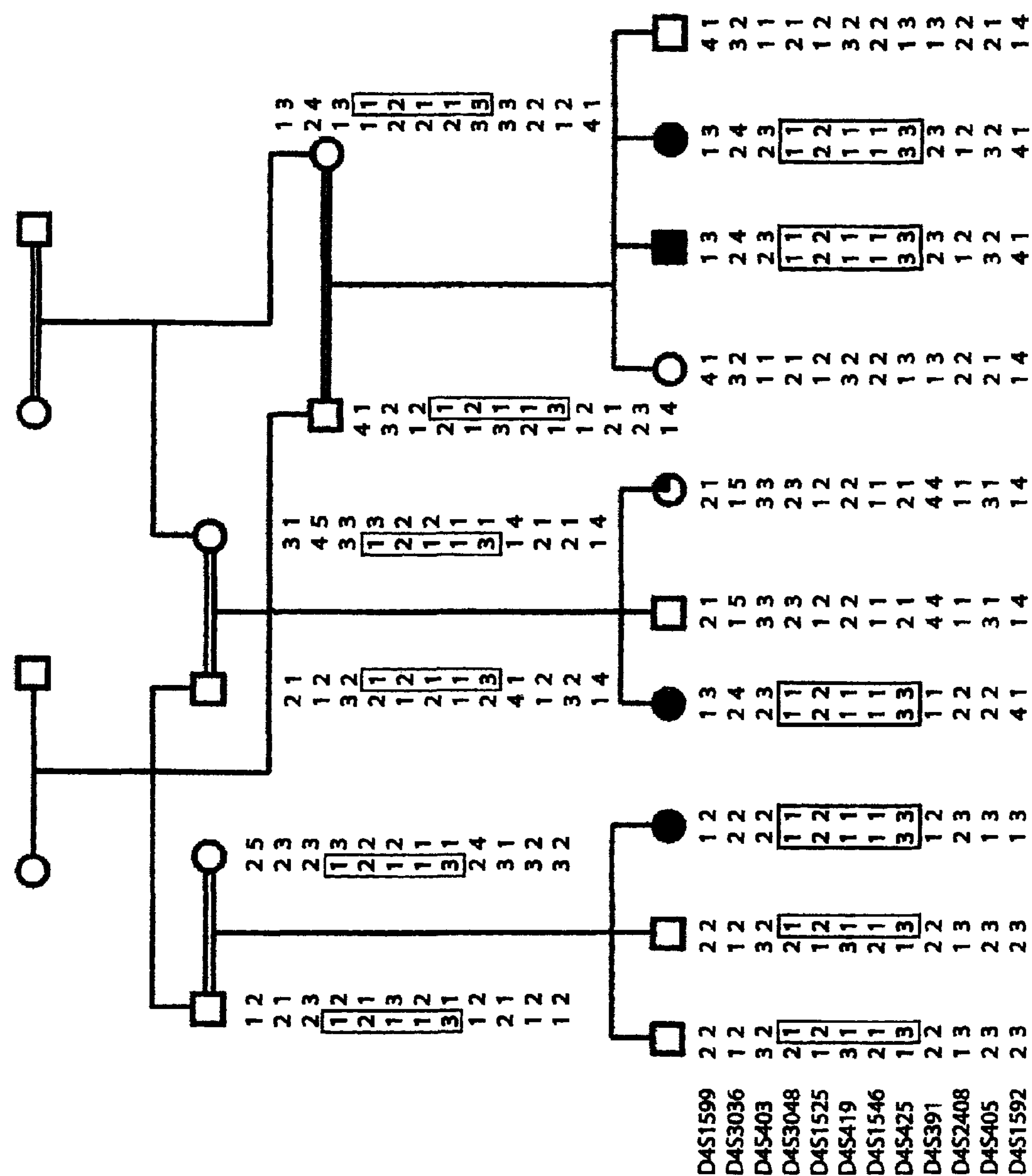
FIG. 4 shows haplotype analysis for the Mianwali family.

The following description is of a preferred embodiment.

We have identified by homozygosity mapping followed by mutation screening a new gene involved in autosomal recessive mental retardation plus retinitis pigmentosa. The gene, CC2D2A (also termed KIAA1345; NCBI MIM entry 612013; contains a C2 domain near the C-terminal region of the protein, in addition to coiled-coil regions. The C2 motif is thought to be involved in calcium dependent phospholipid binding. CC2D1A, one of the three previously identified ARMR genes, also contains a single C2 domain towards the C-terminal end of the protein in addition to coiled-coil regions. Without wishing to be bound by theory or limiting in any manner, it is possible that these two proteins may have similar functions, and may be components of the same or parallel pathways that are important components for neuronal development, disruption of which leads to developmental delay.

Proteins and Amino Acids

According to the present invention, there is provided a protein comprising a fragment of SEQ ID NO:7. In a preferred embodiment the protein is truncated at amino acid 779 or earlier. In an alternate embodiment, the protein has all or part of the C2 domain abolished. Other proteins are also contemplated as described herein.

According to the present invention there is provided a protein that terminates in the amino acid sequence defined by DHEGGSGMES (SEQ ID NO:1), more preferably TLDHEGGSGMES (SEQ ID NO:2). The sequence as provided in SEQ ID NO:1 may comprise the C-terminal of a larger protein, for example, but not limited to the proteins defined in SEQ ID NO: 3 or SEQ ID NO:4.

The present invention also contemplates that the protein may comprise a fragment of SEQ ID NO:3, provided that the fragment terminates in the amino acid sequence defined by SEQ ID NO:1, for example, amino acids X-783 of SEQ ID NO:2, wherein X is for example, but not meant to be limiting 2, 5, 10, 20, 50, 100, 150, 200, 250, 300, 350, 400, 450, 500, 550, 600, 650, 700, 710, 720, 730, 740, 750, 760, 770, 772 or any value therein between.

The present invention further contemplates proteins which are between 80% to 100% identical over a span of at least 11 continuous amino acids defined in SEQ ID NO:3 and which terminate in the amino acid sequence defined by DHEGGSGMES (SEQ ID NO:1). For example, the proteins may be 80%, 82%, 84%, 86%, 88%, 90%, 92%, 94%, 96%, 98%, 99%, 99.1%, 99.2%, 99.3%, 99.4%, 99.5%, 99.6%, 99.7%, 99.8%, 99.9% or 100% identical to SEQ ID NO:3 and which terminates in SEQ ID NO: 1 at the C-terminus. Further, the proteins may comprise a percent identity or a range of identities defined by any two values provided above, or any value therein between.

Any method known in the art may be used for determining the degree of identity between polypeptide sequences. For example, but without wishing to be limiting, a sequence search method such as BLAST (Basic Local Alignment Search Tool; (Altschul S F, Gish W, Miller W, Myers E W, Lipman D J (1990) J Mol Biol 215, 403 410) can be used according to default parameters as described by Tatiana et al., FEMS Microbial Lett. 174:247 250 (1999), or on the National Center for Biotechnology Information web page at ncbi.nlm.gov/BLAST/, for searching closely related sequences. BLAST is widely used in routine sequence alignment; modified BLAST algorithms such as Gapped BLAST, which allows gaps (either insertions or deletions) to be introduced into alignments, or PSI-BLAST, a sensitive search for sequence homologs (Altschul et al., Nucleic Acids Res. 25:3389 3402 (1997); or FASTA, which is available on the world wide web at ExPASy (EMBL—European Bioinformatics Institute). Similar methods known in the art may be employed to compare DNA or RNA sequences to determine the degree of sequence identity.

Nucleic Acids

Also contemplated by the present invention is a nucleic acid comprising a sequence a) encoding a protein as defined above, or a fragment thereof;
b) that is the complement of a sequence encoding the protein as defined above, or a fragment thereof,
c) that is capable of hybridizing to a nucleic acid encoding the protein as defined above or fragment thereof under stringent hybridization conditions, or
d) that is capable of hybridizing to a nucleic acid contained within 5' or 3' untranslated regions, intronic sequences, or upstream promoter or other regulatory sequences.

In an embodiment the nucleic acid comprises a nucleotide sequence that encodes the amino acid sequence defined by SEQ ID NO: 1, more preferably SEQ ID NO:2. In still a further embodiment, there is provided a nucleic acid comprising a nucleotide sequence that encodes the amino acid sequence defined by SEQ ID NO:3, SEQ ID NO:4 or a fragment thereof that comprises SEQ ID NO:1. For example, but not wishing to be limiting in any manner, the nucleic acid may comprise SEQ ID NO: 3. These representative sequences are exemplary and are not meant to be exhaustive or limiting in any manner.

In a further embodiment of the present invention, there is provided a nucleic acid of at least about 7 nucleotides which binds to a mutant form of the CC2D2A gene, the mutant form encoding a protein comprising the amino acid sequence defined above, for example SEQ ID NO:1, but that does not bind to the wild-type form of a CC2D2A gene that encodes a protein that terminates in a sequence other than SEQ ID NO:1. For example, but not to be considered limiting in any manner, a mutant form of the CC2D2A gene may comprise SEQ ID NO: 5, and a wild-type form of a CC2D2A gene may comprise SEQ ID NO:6. Such nucleic acids may be used as probes in screening methods to identify subjects that are carriers or that have a genetic mutation associated with mental retardation.

While the present invention contemplates probes comprising nucleotide sequences of at least about 7 nucleotides, preferably the probe comprises greater than 7 nucleotides, for example, but not limited to 9, 11, 15, 17, 21, 25, 27, 30, 40, 50, 100 or more nucleotides. Further the size of the probes may be defined by a range of any two values as provided above or any two values in between. Also, the probe may be labeled by an appropriate moiety as would be known in the art, for example, but not limited to one or more fluorophores, radioactive groups, chemical substituents, enzymes, antibodies or the like to facilitate identification in hybridization assays and other assays or tests.

The nucleic acids as provided herein may be employed to produce proteins which are associated with mental retardation, as probes to identify or diagnose subjects with mental retardation, identify or diagnose subjects carrying a mutation which causes or predisposes the subject or its offspring to mental retardation, antisense or short inhibitory RNA that may be used to modulate production of protein from genes associated with mental retardation or a combination thereof.

The present invention contemplates nucleic acids that hybridize to nucleotide sequences that encode proteins as provided herein under stringent hybridization conditions. Stringent hybridization conditions as described above may be, for example but not limited to hybridization overnight (from about 16-20 hours) hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours); or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each for unique sequence regions.

The present invention is further directed to a nucleotide construct comprising the nucleic acid as described above operatively linked to one or more regulatory elements or regulatory regions. By "regulatory element" or "regulatory region", it is meant a portion of nucleic acid typically, but not always, upstream of a gene, and may be comprised of either DNA or RNA, or both DNA and RNA. Regulatory elements may include those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. By a nucleotide sequence exhibiting regulatory element activity it is meant that the nucleotide sequence when operatively linked with a coding sequence of interest functions as a promoter, a core promoter, a constitutive regulatory element, a negative element or silencer (i.e. elements that decrease promoter activity), or a transcriptional or translational enhancer.

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

Regulatory elements as used herein, also includes elements that are active following transcription initiation or transcription, for example, regulatory elements that modulate gene expression such as translational and transcriptional enhancers, translational and transcriptional repressors, and mRNA stability or instability determinants. In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, may be operatively associated (operatively linked) with heterologous regulatory elements or promoters in order to modulate the activity of the heterologous regulatory element. Such modulation includes enhancing or repressing transcriptional activity of the heterologous regulatory element, modulating post-transcriptional events, or both enhancing/repressing transcriptional activity of the heterologous regulatory element and modulating post-transcriptional events. For example, one or more regulatory elements, or fragments thereof, may be operatively associated with constitutive, inducible, tissue specific promoters or fragment thereof, or fragments of regulatory elements, for example, but not limited to TATA or GC sequences may be operatively associated with the regulatory elements of the present invention, to modulate the activity of such promoters within plant, insect, fungi, bacterial, yeast, or animal cells.

There are several types of regulatory elements, including those that are developmentally regulated, inducible and constitutive. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within a plant as well.

By "promoter" it is meant the nucleotide sequences at the 5' end of a coding region, or fragment thereof that contain all the signals essential for the initiation of transcription and for the regulation of the rate of transcription. There are generally two types of promoters, inducible and constitutive promoters.

An inducible promoter is a promoter that is capable of directly or indirectly activating transcription of one or more DNA sequences or genes in response to an inducer. In the absence of an inducer the DNA sequences or genes will not be transcribed. Typically the protein factor that binds specifically to an inducible promoter to activate transcription is present in an inactive form which is then directly or indirectly converted to the active form by the inducer. The inducer can be a chemical agent such as a protein, metabolite, growth regulator, or a physiological stress imposed directly by heat, cold, or toxic elements or indirectly through the action of a pathogen or disease agent such as a virus.

A constitutive promoter directs the expression of a gene throughout the various parts of an organism and/or continuously throughout development of an organism. Any suitable constitutive promoter may be used to drive the expression of the proteins or fragments thereof as described herein. Examples of known constitutive promoters include but are not limited to those associated with the CaMV 35S transcript. (Odell et al., 1985, *Nature,* 313: 810-812).

The term "constitutive" as used herein does not necessarily indicate that a gene is expressed at the same level in all cell types, but that the gene is expressed in a wide range of cell types, although some variation in abundance is often observed.

The gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3 prime end of the mRNA precursor.

The gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

The present invention further includes vectors comprising the nucleic acids as described above. Suitable expression vectors for use with the nucleic acid sequences of the present invention include, but are not limited to, plasmids, phagemids, viral particles and vectors, phage and the like. For insect cells, baculovirus expression vectors are suitable. For plant cells, viral expression vectors (such as cauliflower mosaic virus and tobacco mosaic virus) and plasmid expression vectors (such as the Ti plasmid) are suitable. The entire expression vector, or a part thereof, can be integrated into the host cell genome.

Those skilled in the art will understand that a wide variety of expression systems can be used to produce the proteins or fragments thereof as defined herein. With respect to in vitro production, the precise host cell used is not critical to the invention. The proteins or fragments thereof can be produced in a prokaryotic host (e.g., *E. coli* or *B. subtilis*) or in a eukaryotic host (e.g., *Saccharomyces* or *Pichia*; mammalian cells, such as COS, NIH 3T3, CHO, BHK, 293, or HeLa cells; insect cells; or plant cells). The methods of transformation or transfection and the choice of expression vector will depend on the host system selected and can be readily determined by one skilled in the art. Transformation and transfection methods are described, for example, in Ausubel et al. (1994) Current Protocols in Molecular Biology, John Wiley & Sons, New York; and various expression vectors may be chosen from those provided, e.g., in Cloning Vectors: A Laboratory Manual (Pouwels et al., 1985, Supp. 1987) and by various commercial suppliers.

In addition, a host cell may be chosen which modulates the expression of the inserted sequences, or modifies/processes the gene product in a specific, desired fashion. Such modifications (e.g., glycosylation) and processing (e.g., cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed protein.

Methods of Screening

The present invention also provides a method of screening a subject for a gene sequence associated with mental retardation, the method comprising, a) obtaining a biological sample from the subject, the biological sample comprising DNA or RNA, and;

b) assaying the sample for one or more mutations in a nucleotide sequence encoding a CC2D2A protein as defined by SEQ ID NO:7, an isoform or a naturally occurring allelic variant thereof, wherein the presence of said one or more mutations results in deletion in one or more amino acids of the protein or premature truncation of the protein and indicates that the subject has a gene sequence associated with mental retardation.

In the method as defined above, the one or more mutations include without limitation, deletions, inversions, translocations, duplications, splice-donor site mutations, point-mutations or the like. The one or more mutations may occur in any region of the protein, for example, exon 1, 2, 3, 4, 5, 6, 7, 8, 9, 10, 11, 12, 13, 14, 15, 16, 17, 18, 19, or higher. In a preferred embodiment, the one or more mutations occur in exon 19. In an alternate embodiment, the one or more mutations abolish all or part of the C2 domain, for example, between 5% and 100% of the C2 domain including 10%, 20%, 30%, 40%, 50%, 60%, 70%, 80%, 90% or 100% thereof. In still a further embodiment, the one or more mutations result in truncation of the CC2D2A protein as defined by SEQ ID NO:7 in the C2 domain, for example, but not limited to at about amino acid 779. However, without wishing to be limiting in any manner, the present invention contemplates premature truncation at any earlier or later amino acid in the sequence.

The present invention also provides a method of screening a subject for a gene sequence associated with mental retardation, the method comprising, a) obtaining a biological sample from the subject, the biological sample comprising DNA or RNA, and;

b) assaying the sample for one or more mutations the gene sequence encoding CC2D2A protein as defined by SEQ ID NO:6, an isoform or a naturally occurring allelic variant thereof, wherein the presence of said one or more mutations results in deletion in one or more amino acids of the protein or premature truncation of the protein and indicates that the subject has a gene sequence associated with mental retardation.

The present invention also provides a method of screening a subject for a gene sequence associated with mental retardation, the method comprising a) obtaining a biological sample from the subject, the biological sample comprising DNA or RNA, and;

b) assaying the sample for a nucleic acid encoding a protein comprising SEQ ID NO:1 at the C-terminus, wherein the presence of the nucleic acid indicates that the subject has a gene sequence associated with mental retardation.

It is to be understood in the method as described above, that step b) may comprise assaying for a nucleic acid encoding a protein comprising SEQ ID NO:2, SEQ ID NO:3, SEQ ID NO:4 or a fragment thereof.

By the terms "assaying the sample" it is meant characterizing the sample provided by the subject for a nucleic acid that encodes a protein as defined above and is meant to include without limitation hybridization assays, nucleotide sequencing, nucleotide PCR including, but not limited to RT-PCR, etc or any combination thereof.

The sample obtained from the subject may comprise any tissue or biological fluid sample from which DNA or RNA may be obtained. For example, but not wishing to be limiting, DNA may be obtained from blood, hair follicle cells, skin cells, cheek cells, saliva cells, tissue biopsy, or the like. In a preferred embodiment, the sample is blood.

The present invention also contemplates screening methods which identify and/or characterize the proteins as defined above within biological samples from subjects. Such samples may or may not comprise DNA or RNA. For example, such screening or testing methods may employ immunological methods, for example, but not limited to antibody binding assays such as ELISAs or the like, protein sequencing, electrophoretic separations to identify the proteins as described above in a sample. As will be evident to a person of skill in the art, the screening methods allow for the differentiation of the proteins as defined herein from wild type proteins known in the art.

Accordingly, in a further embodiment, the present invention also provides a method of screening a subject for mutant protein associated with mental retardation, the method comprising a) obtaining a biological sample from the subject, b) testing the sample for a protein that comprises SEQ ID NO:1 at the C-terminus thereof, wherein the presence of the protein indicates that the subject has a gene sequence that expresses a mutant protein associated with mental retardation.

It is to be understood in the method as described above, that step b) may comprise testing for a protein comprising SEQ ID NO:2, SEQ ID NO:3, SEQ ID NO:4 or a fragment thereof.

Kits

Also provided by the present invention is a kit comprising a protein as provided herein, for example, but not limited to one that comprises SEQ ID NO:1 at the C-terminus thereof, and that is associated with mental retardation, an antibody that selectively binds to a protein as provided herein, for example, but not limited to one that comprises SEQ ID NO:1 at the C-terminus thereof, and that is associated with mental retardation, rather than a similar wild-type protein that is not associated with mental retardation, one or more nucleic acid primers to amplify a nucleotide sequence encoding a protein or fragment thereof which comprises a mutation associated with mental retardation as provided herein, one or more nucleic acid probes of between about 9 and 100 nucleotides that hybridize to the nucleotide sequence encoding a protein or fragment thereof which comprises a mutation associated mental retardation as provided herein, one or more reagents including, but not limited to buffer(s), dATP, dTTP, dCTP, dGTP, DNA polymerase(s), instructions for assaying, diagnosing or determining the presence of a nucleotide sequence or protein in a subject that is associated with mental retardation, instructions for using any component or practicing any method as described herein, or any combination thereof.

The present invention will be further illustrated in the following examples.

EXAMPLES

Example 1

Materials and Methods

Patients

The family ascertained in this study is from the province of Punjab in Pakistan. Appropriate informed consent was obtained from all participants in the study. Clinical examination of affected individuals revealed that the early motor development was delayed, occipito-frontal circumference (OFC) was within normal range and face appears normal. There was no dysmorphic feature, no hepatosplenomegaly, no murmur, and no skin abnormalities. Structural MRI of the brain was performed for two affected individuals, which was generally normal, with some indication of mild cerebellar atrophy in one of the affected individuals. Molar-toot sign (MTS) was also present—a hallmark sign of Joubert syndrome.

Sample Collection and DNA Extraction

Blood samples were collected from five affected and 12 unaffected members of the family. Genomic DNA was extracted from peripheral blood leukocytes by standard methods. Lymphoblast cell line was successfully established for only one family member.

SNP Homozygosity or Autozgosity Mapping

DNA samples of five affected and one unaffected were analyzed using the Affymetrix GeneChip Mapping 500K array. These arrays allow analysis of ~500,000 SNPs with a median physical distance of 2.5 kb and an average physical distance of 5.8 Kb between SNPs. The average heterozygosity of these SNPs is 0.30. However, in our experiments we just used NspI chip from GeneChip Mapping 500K set which allowed us to genotyping ~260,000 SNPs in our samples. Sample processing, labelling and hybridization were performed in accordance with the manufacturer's instructions (Affymetrix Mapping 500K Assay Manual). The arrays were scanned with a GeneChip Scanner and the data was processed using GeneChip® Operating Software (GCOS) and GeneChip® Genotyping Analysis Software (GTYPE) Software (ver. 3.0.2) to generate SNP allele calls.

Copy Number Analysis

Copy Number variations (CNVs) that include deletions, and duplication events were inferred by comparative analysis of hybridization intensities using dChip analyzer (Li and Wong, 2003; Zhao, 2004, Zhao, 2005). After normalization, we used Hidden Markov Model (HMM) to infer the DNA copy number from the raw signal data.

DNA Analysis with Microsatellite Markers and Linkage Analysis 12 fluorescent labelled microsatellite markers across the 4p region were PCR amplified using standard protocol and were electrophoresed on an ABI 3730x1 DNA analyzer. The genotypes were called using Genemapper software (Applied Biosystems) and linkage analysis was performed using MLINK software.

Cytogenetic Analysis

Karyotyping was performed by harvesting the lymphoblast cell line using standard cytogenetic procedure. Slides were made from fixed cells in the Thermotron, aged and then GTG banded.

DNA Sequencing and Mutation Screening

PCR primers were designed using Primer 3 (v. 0.3.0) to amplify all exons and intron-exon boundaries of known genes within the critical region. PCRs were performed using standard conditions, and products were purified and sequenced directly using the BigDye Terminator v3.1 Cycle Sequencing Ready Reaction Kit (Applied Biosystems)

Expression Analysis

Expression analysis for the CC2D2A gene was performed by RT-PCR, using the forward primer from exon 18 (5'-ACAGTCAGTCGGCCACTAGG) (SEQ ID NO:8) and reverse primer from exon 25 (5'-GTTCTGCCAGCTTGAAAAGG) (SEQ ID NO:9), thus spanning exon 19 containing the splice mutation in the Mianwali family.

Bioinformatic Analysis of CC2D2A

Promoter analysis for CC2D2A was performed using PromoterInspector from Genomatix. Homology searches was performed using the BLAST algorithm at the National Center for Biotechnology Information (Altschul et al. 1997) and the UCSC Human Genome Project Working Draft. (Protein domain predictions were performed using the SMART program (Simple Modular Architecture Research Tool) from the European Molecular Biology Laboratory (EMBL), the PSORT II suite of programs at University of Tokyo, the SOSUI algorithm and the COILS Program from the Swiss EMBNet. In order to identify regions of the proteins that have been highly conserved across evolution so that additional potentially functional relevant motifs may be identified in CC2D2A, comparative sequence analysis was performed for CC2D2A orthologues (known and predicted from genomic or cDNA sequences) across a variety of species using CLUSTAL-W.

Results

The locus for mental retardation and retinitis pigmentosa, as described herein and throughout has been accorded MIM entry 612285 at NCBI.

Homozygosity Mapping/Autozygosity Mapping

Homozygosity mapping (Autozygosity mapping) revealed a common ~11.2 Mb homozygous and haploidentical region on short arm of chromosome 4 (4p15.2-p15.33) in four affected individuals but not in the normal individual, nor in the fifth affected individual. This was the only large (>0.5 Mb) homozygous and haploidentical region present in four out of five affecteds, and no such regions were present in all five. The 11.2 Mb critical region containing ~39 genes (UCSC Genome Browser) was fine mapped by sequencing the flanking SNPs, rs2191685 and rs7664104 (at 14.001 and 25.203 Mb from the p telomere respectively (UCSC March 2006).

Copy Number Variants (CNVs) Analysis

As homozygosity mapping (autozygosity mapping) did not reveal any common region in all the affected individuals, we further hypothesized that there might be a large chromosomal deletion or duplication segregating with phenotype. Interestingly, copy number analysis indicated duplication of entire X chromosome in the fifth affected individual, who did not share the disease haplotype with other four affected members of the family. Subsequent cytogenetic analysis has indicated the karyotype 48,XXXX. This rare tetrasomy is almost always associated with mental retardation, and thus suggests that this female is a phenocopy.

Linkage Analysis

Linkage to the locus on chromosome 4p15.33-p15.2 was confirmed by genotyping 17 members of the family using the 12 microsatellite markers across the 4p region. Linkage was calculated using MLINK software, and a maximum two-point logarithm of odds (LOD) score of 3.59 at theta=0.0 was obtained at marker D4S419.

Mutation Screening

The 11.2 Mb critical region contains about 39 annotated genes (UCSC 2004). Because the gene for phenylketonuria type 2 (PKU2; MIM+262630), quinoid dihydropteridine reductase (QDPR), lies within the critical region, we initially, considered this as a potential candidate gene, and hence we screened all the coding sequence and splice sites of QDPR. An upstream homozygous base substitution was identified, but this was also homozygous in one of the unaffected parents, so did not segregate with disease. Furthermore, biochemical analysis of patient's blood samples also excluded this gene. By sequence analysis of all other known genes in the region, a splice donor site mutation (IVS19+1:G to C) in exon 19 of the CC2D2A genes was identified. The mutation segregates with phenotype and is predicted to result in addition of 3 nonsense aminoacids (M, E, S) and then premature truncation of protein. The CC2D2A (NM_001080522) gene gives a mRNA ~5 Kb in length, and consists of at least 13 different isoforms with up to 37 exons spanning ~131.5 Kb of genomic DNA (from 15,080,760-15,212,278 bp; UCSC March 2006) on 4p15.33. The CC2D2A protein contains up to 1620 amino acids (depending on exon usage) and a C2 domain is predicted in this gene from 1042-1202. From RT-PCR followed by sequence analysis using lymphoblast-derived cDNA from the affected individuals, we determined that the splice mutation results in the skipping of exon 19. The splicing of exon 18 to exon 20 results in a frame shift, with 13 nonsense amino acids added (ECPSHLKLMAVTS*) beyond exon 18 before a premature stop codon truncates the protein at amino acid 740, thus abolishing the C2 domain. We screened 460 chromosomes of healthy controls, also from Pakistan, and were unable to identify find this mutation.

Bioinformatic Analysis of the CC2D2A Gene and Encoded Protein

Figure 5:
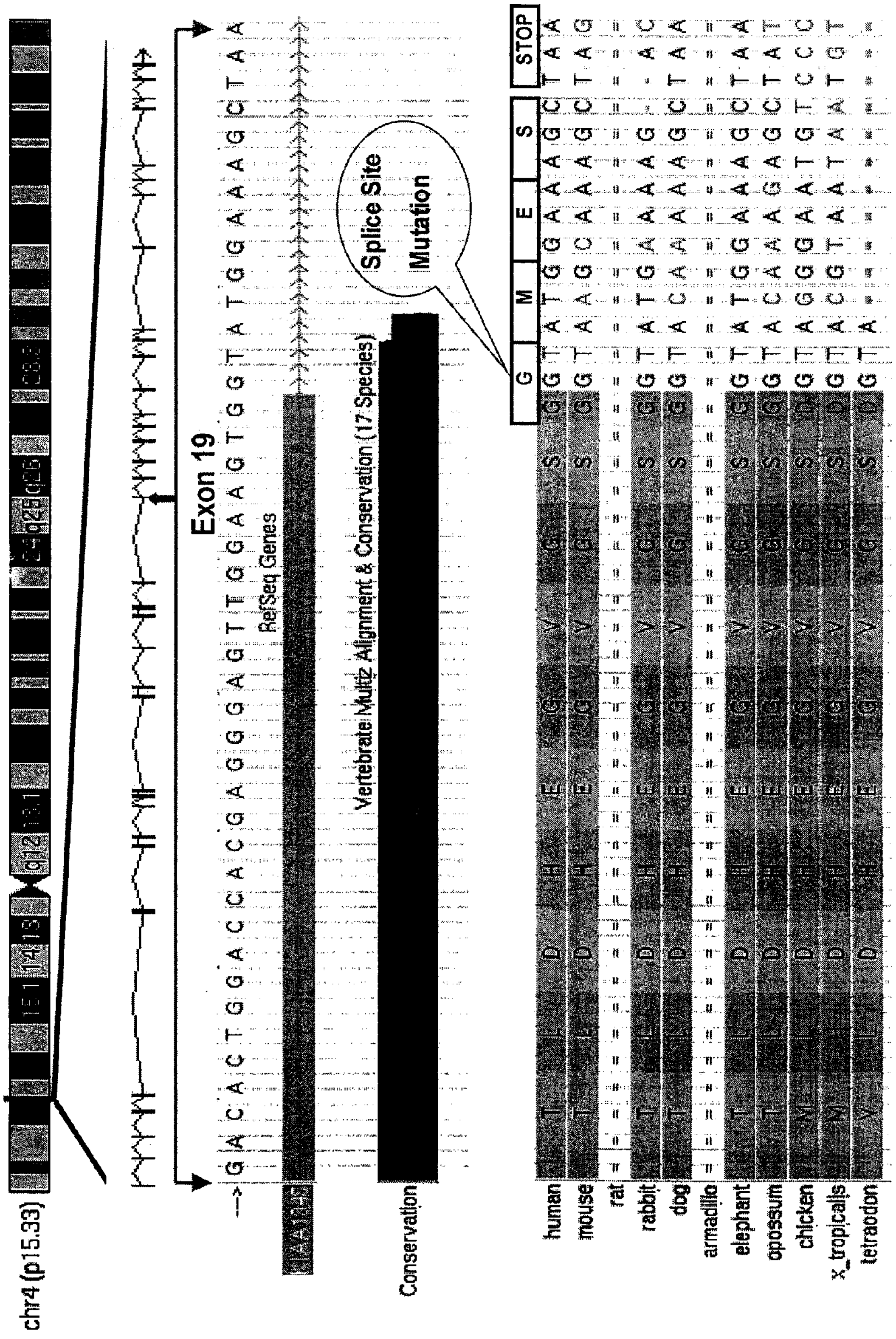
FIG. 5 shows an ideogrammatic representation of the mutation region in the CC2D2A gene.
Figure 6:
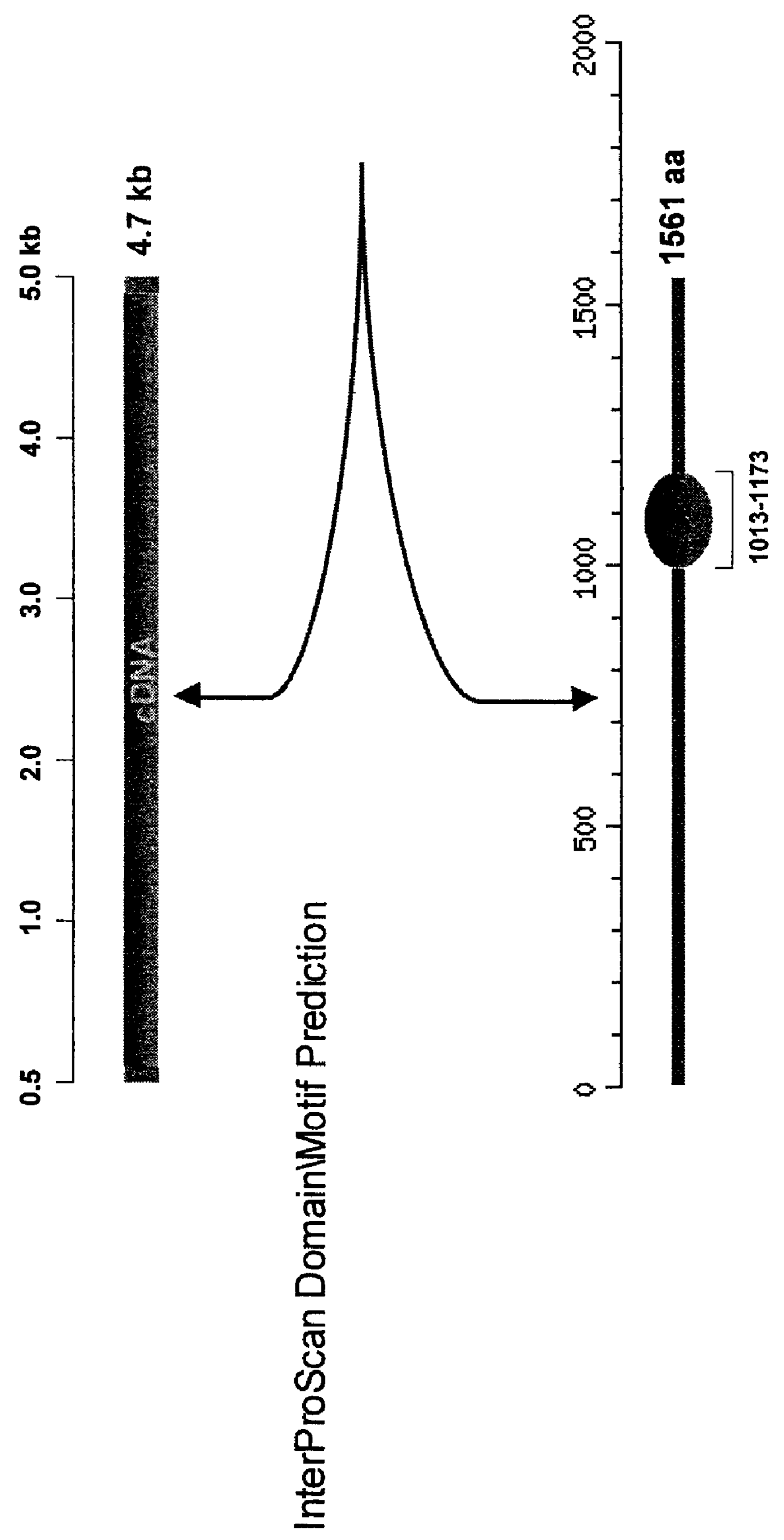
FIG. 6 shows an ideogrammatic representation of the CC2D2A cDNA and the encoded protein.

Genomic organization of CC2D2 A on 4p 15.33 is shown in FIG. 5. Analysis of the sequence at and around the CC2D2A gene using the ElDorado and Promoterinspector programs from Genomatix indicated the presence of a putative promoter sequence of 773 bp from 15,080,088-15,080,860 bp (from the 4p telomere; UCSC March 2006). Analysis of the protein sequence using Simple Modular Architecture Research Tool (SMART) indicated the presence of a C2 domain from residue 1042 to 1202 (in the 1620 amino acid isoform). The C2 domain, also known as protein kinase C conserved region 2 (CalB), is a $Ca^{2+}$-dependent membrane-targetting module present in many proteins involved in membrane trafficking or signal transduction. Transmembrane (TM) prediction using TMpred suggested two possibilities, either 1 strong TM helix (from residues 1278 to 1297), or no clear TM domains. Coiled-coil analysis using COILS v.21 predicted three stretches of the protein with >90% probability of coiled-coil structure: amino acid residues 442-463, 472-492 and 533-580 (using a 21-residue window). SOSUI predicts the protein to be soluble, with average hydrophobicity of −0.655. No signal peptide was identified, and k-NN prediction suggests a nuclear localization within the cell (91.3% nuclear, 4.3% cytoskeletal, 4.3% plasma membrane). Secondary structure is predicted to be mainly alpha helix and random coil, with some extended strand (Network Protein Sequence analysis). No signal peptides were detected, hi addition, initial analysis indicates that CC2D2A appears to have a number of potential CaMKII recognition sites (9 RXXS/T and 3 S/TXD sites), as well as numerous putative PKC phosphorylation sites. Two putative nuclear localization signals were also detected using the PredictProtein suite (QRAKKKKRK (SEQ ID NO: 12) at residue 587 and RPRRK (SEQ ID NO: 13) at 1021). Alignment analysis indicates no homology with CC2D1 A and IB. There is 34% homology with CC2D2B, but only towards the C-terminal end (residues 1250-1620) of CC2D2A. CC2D2B has neither coiled coil nor C2 domains.

Comparative Sequence Analysis of CC2D2A

We performed cross-species sequence analysis using either full length coding sequences, or orthologues predicted from genomic DNA sequence and expressed sequenced tags (EST) from 18 species. Comparative analysis of the protein sequence using CLUSTALW shows a high degree of conservation across vertebrate evolution (FIG. 5). The human sequence is 99.4% identical to that of chimp, 96.9% to rhesus monkey, 88.8% to horse, 84.8% to mouse and rat, 75.7% to opossum, 70.7% to chicken, 60% to xenopus, 59.6% to zebrafish, 44.7% to sea urchin. The human protein is 21.6% identical to *C. elegans* protein K07G5.3 (NP_492026), and 29.9% with the *Drosophila* protein CG18631 (NP_611230), with the strongest overlap and homology occurring towards the C-terminal end (from amino acid 1301 in human, 894 in *C. elegans*, and 200 in *Drosophila*, to the carboxyl terminus), suggesting conserved functionality to this region in addition to the C2 domain. The WormBase information on this protein indicates that it is expressed in the nervous system, including head and tail neurons (as well as other unidentified cells in the head and tail) during both adult and larval stages. Knockdown through RNAi of the K07G5.3 gene was non-lethal.

The Ka/Ks ratio calculated from pairwise comparisons of the full-length cDNA sequence across species revealed that overall, the CC2D2A gene sequence is conserved. Interspecies comparisons of closely related species also revealed a high level of overall conservation. Ka and Ks values calculated from pairwise comparisons of the C2 domain in primates were higher than the Ka and Ks for the full-length primate sequence comparisons. In contrast, the mouse-rat C2 domain comparison gave a Ka value that was lower than the Ka for the full length mouse-rat comparison. However, the Ks value was slightly higher for the rodent C2 domain than for the rodent full length sequence. To further examine whether the C2 domain had a different evolutionary profile than the flanking sequences, 500 basepairs upstream and downstream of this region (Flanking Regions 1 and 2, hereafter FR1 and FR2) were analyzed in pairwise comparisons. In the primate lineage of human, chimp and rhesus, both the Ka and Ks values were higher for the C2 domain than for FR1 or FR2. In the mouse-rat comparison, the Ka for the C2 domain was lower than the Ka for both FR1 and FR2, while the Ks for the C2 domain was higher than the Ks for FR1, but similar to that for FR2.

The C terminal domain (encompassing the last 1113 nucleotides of the coding sequence in the human) was then compared with the first 1115 nucleotides at the N terminal domain, in order to examine the rates of evolution at the conserved C terminal. In all pairwise comparisons, the Ka/Ks ratios for the C terminal were significantly lower than for the N terminal, providing additional evidence that the C terminal is well conserved across species.

Expression Analysis

Figure 7:
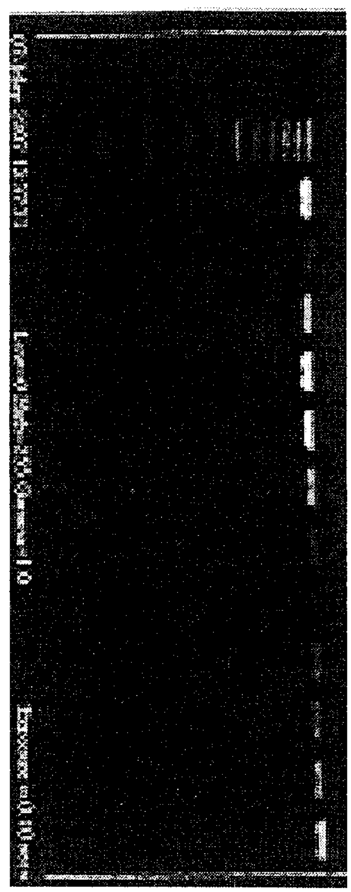
FIG. 7 shows the express of the CC2D2A gene in several tissues.
Figure 8:
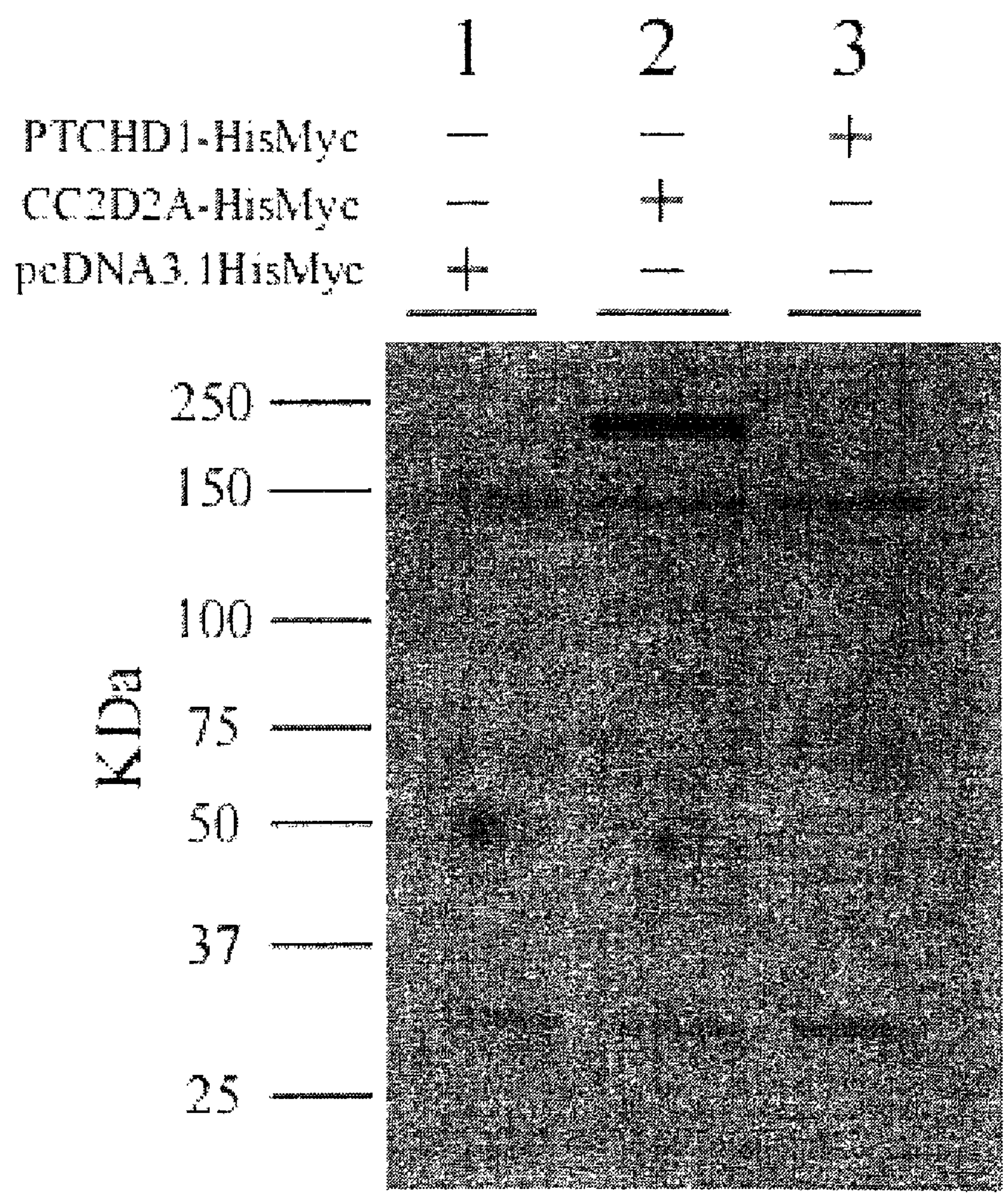
FIG. 8 shows results that anti-serum from rabbit recognizes recombinant CC2D2A. Cos-7 cells were transfected with empty vector (1), CC2D2AHisMyc (2) or PTCHD1HisMyc (3). A strong band is seen in lane 2 between 150 and 250 Kda but is not detected in control lanes 1 and 3. The theoretical size is 191 kDa (186 kDa CC2D2A plus 6 kDa HisMyc tag). Anti-serum was diluted 1:500 in 0.1% TBS-T in 5% milk. Secondary antibody was anti-rabbit IgG HRP (Jackson immunoresearch) diluted 1:20 000.

RT-PCR analysis indicates that CC2D2A is expressed in many tissues (FIG. 7). In a panel of cDNAs from 12 tissues expression was detected in each tissue, albeit at varying levels, with maximum expression seen in prostate, pancreas, kidney, lung and liver, with lower expression in spleen, small intestine, colon, skeletal muscle, ovary, thymus and heart. Brain expression was also strong. Further, expression of the CC2D2A-GFP fusion protein in Cos-7 cells appeared to be almost exclusively cytoplasmic, despite the predicted presence of potential nuclear localization signals.

Antibody to CC2D2A

The anti-CC2D2A antibodies were raised against 2 epitopes injected into rabbits carried out as a service by OPEN Biosystems (Huntsville, Ala.). Two epitopes were utilized due to the sheer size of the predicted CC2D2A protein ~186 kDa. The sequence utilized was from human sequence of CC2D2A (NP_001073991). The first epitope is in the centre but N-terminal to the Coiled-Coil and C2 Domain, RSKRFRLLHLRSQEVPEFRNYK (SEQ ID NO:10), as well as the mutation in the Mianwali family, whereas the second epitope is on the C-terminal tail, EDDHRAELLKQLGDYRFSGFPL (SEQ ID NO:11). These epitopes are also 100% conserved in the mouse orthologue of CCD2A (NP_758478) making the anti-bodies potentially cross reactive for human and mouse CC2D2A. The rabbit anti-serum was purified using affinity purification.

Example 2

CC2D2A in Relation to Joubert Syndrome

We have reported the identification through homozygosity/autozygosity mapping followed by gene sequencing in a Pakistani family with mental retardation and retinitis pigmentosa of a truncating mutation within the gene CC2D2A. Without wishing to be limiting or bound by theory, it is also believed that the symptoms in this family overlap with Joubert syndrome (MIM 213300).

Joubert syndrome, also known as Joubert-Boltshauser syndrome, JS, is a rare autosomal recessive disorder first described in a French-Canadian family (Joubert et al, 1969). JS is a clinically and genetically heterogeneous group of disorders characterized by hypoplasia of the cerebellar vermis with the hallmark neuroradiologic "molar tooth sign" (MTS), and accompanying neurologic symptoms, including abnormal breathing pattern and developmental delay. Other variable features include nystagmus, retinal dystrophy, dysmorphic facial features, hypotonia, ataxia, occipital encephalocele, renal disease, oculo colobomas, hepatic abnormalities and polydactyl). Characteristic dysmorphic facial features often noted are described as: large head, prominent forehead, high rounded eyebrows, epicanthal folds, ptosis (occasionally), upturned nose with evident nostrils, open mouth (the mouth tends to have an oval shape early on, a 'rhomboid' appearance later, and finally can appear triangular with downturned mouth angles), tongue protrusion and rhythmic tongue motions, and occasionally low-set and tilted ears (Maria et al, 1999). Neuroopthalmologic examination shows oculomotor apraxia.

MTS has been observed in a group of syndromes now termed Joubert syndrome and related disorder (JSRD). JSRD includes the following:

1. classical JS (MIM213300)
2. JS plus Leber congenital amaurosis (LCA)
3. JS plus nephronophthisis (NPHP [MIM 256700]
4. JS plus LCA plus NPHP (also termed cerebello-oculorenal syndrome, CORS, MIM 608091)
5. cerebellar vermis hypo/aplasia, oligophrenia, congenital ataxia, ocular coloboma, hepatic fibrosis (COACH [MIM 216360]) syndrome
6. oral-facial-digital syndrome type VI (MIM 277170)

and other features such as polydactyl)- and encephalocele also present in each of the six subgroups.

Many genes identified for JSRD localize to cilia, and thus JSRD is thought to be a disorder of cilia function, or ciliopathy. JSRD mutations have been found in AHI1, CEP290, NPHP1, RPGRIP1L, TMEM67 and ARL13B.

In addition, another syndrome, Meckel syndrome (also known as Meckel-Gruber syndrome; MKS; MIM 249000) shares some of the clinical features of JSRD, Mutations causing MKS have been found in TMEM67, RPGRIPL1, and now in CC2D2A (Tallila et al, 2008). MKS is generally lethal.

In terms of prevalence of JS, in the United States this has been estimated as approximately 1:100 000 (Parisi et al, 1999-2006), although this is likely to be an underestimate, as the clinical signs or MRI findings are poorly recognised and diagnosed, particularly in the more mildly affected individuals (Parisi et al, 2007).

Two of the four affected members of the Pakistani family (the oldest (male, 27 yrs), and the youngest (female, 18 months) underwent full neurological examination and MRI by an independent physician. Whilst many of the JSRD features were not noted, the physician did report the presence of MTS in the MRI of the young girl, and suggested Joubert syndrome as a diagnosis, but excluded because of the lack of other features. Subsequently, all 4 affected members of the family were seen by an ophthalmologist, as the eldest male clearly had visual impairment including night blindness. All 4 showed nystagmus. The elder 3 had night blindness, and progressive retinitis pigmentosa. The youngest (just 3 years at examination) had astigmatism.

The disorder in this family appears related to Joubert syndrome, having the hallmark MTS, mental retardation, nystagmus and retinopathy (and ataxia and cerebellar atrophy, at least in the older patient examined). Thus, in an embodiment of the present invention, there is provided a method of screening a subject for Joubert Syndrome or a nucleotide sequence associated with Joubert Syndrome by assaying for a nucleic acid or protein as described herein. Early diagnosis or identifying subjects at risk for Joubert Syndrome is desirable as many of the symptoms associated with Joubert Syndrome can be treated and/or inhibited by therapeutic intervention.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Basel-Vanagaite, L.; Attia, R.; Yahav, M.; Ferland, R. J.; Anteki, L.; Walsh, C. A.; Olender, T.; Straussberg, R.; Magal, N.; Taub, E.; Drasinover, V.; Alkelai, A.; Bercovich, D.; Rechavi, G.; Simon, A. J.; Shohat, M. (2006). The CC2D1A, a member of a new gene family with C2 domains, is involved in autosomal recessive non-syndromic mental retardation. J. Med. Genet. 43:203-210.

Cantagrel V, Silhavy J L, Bielas S L, Swistun D, Marsh S E, Bertrand J Y, Audollent S, Attié-Bitach T, Holden K R, Dobyns W B, Traver D, Al-Gazali L, Ali B R, Lindner T H, Caspary T, Otto E A, Hildebrandt F, Glass I A, Logan C V, Johnson C A, Bennett C, Brancati F; International Joubert Syndrome Related Disorders Study Group, Valente E M, Woods C G, Gleeson J G. Mutations in the cilia gene ARL13B lead to the classical form of Joubert syndrome. Am J Hum Genet. 2008 August; 83(2):170-179.

Chelly J, Khelfaoui M, Francis F, Chemf B, Bienvenu T (2006). Genetics and pathophysiology of mental retardation. Eur J Hum Genet. 14:701-713.

Curry C J. (2002). Rational evaluation of the adolescent with mental retardation. Adolesc Med13:331-343, vii. Review.

Higgins, J. J.; Pucilowska, J.; Lombardi, R. Q.; Rooney, J. P. (2004). A mutation in a novel ATP-dependent Lon protease gene in a kindred with mild mental retardation. Neurology 63:1927-1931.

Joubert M, Eisenring J J, Robb J P, Andermann F. Familial agenesis of the cerebellar vermis. A syndrome of episodic hyperpnea, abnormal eye movements, ataxia, and retardation. Neurology. 1969 September; 19(9):813-25.

Maria, B. L.; Boltshauser, E.; Palmer, S. C.; Tran, T. X.: Clinical features and revised diagnostic criteria in Joubert syndrome. J. Child Neurol. 14: 583-591, 1999

Molinari, F.; Rio, M.; Meskenaite, V.; Encha-Razavi, F.; Auge, J.; Bacq, D.; Briault, S.; Vekemans, M.; Munnich, A.; Attie-Bitach, T.; Sonderegger, P.; Colleaux, L. (2002). Truncating neurotrypsin mutation in autosomal recessive nonsyndromic mental retardation. Science 298:1779-1781.

Murphy C C Boyle C, Schendel D, Decouflé P, Yeargin-Allsopp M (1998). Epidemiology of mental retardation in children. Ment Retard Dev Diabil Res Rev 4:6-13.

Najmabadi H, Motazacker M M, Garshasbi M, Kahrizi K, Tzschach A, Chen W, Behjati F, Hadavi V, Nieh S E, Abedini S S, Vazifehmand R, Firouzabadi S G, Jamali P, Falah M, Seifati S M, Gruters A, Lenzner S, Jensen L R, Ruschendorf F, Kuss A W, Ropers H H: Homozygosity mapping in consanguineous families reveals extreme heterogeneity of non-syndromic autosomal recessive mental retardation and identifies 8 novel gene loci. Hum Genet 2007; 121:43-48

Noor, A.; Windpassinger, C.; Patel, M.; Stachowiak, B.; Mikhailov, A.; Azam, M.; Irfan, M.; Siddiqui, Z. K.; Naeem, F.; Paterson, A. D.; Lutfullah, M.; Vincent, J. B.; Ayub, M. "CC2D2A, encoding a coiled-coil and C2 domain protein, causes autosomal-recessive mental retardation with retinitis pigmentosa." Am. J. Hum. Genet. 82: 1011-1018, 2008. PubMed ID: 18387594.

Parisi M A, Glass I A: Joubert syndrome; In: GeneReviews at GeneTests-GeneClinics: Medical Genetics Information Resource [database online]. Copyright, University of Washington, Seattle. 1997-2006.

Parisi M A, Doherty D, Chance P F, Glass I A. Joubert syndrome (and related disorders) (OMIM 213300). Eur J Hum Genet. 2007 May; 15(5):511-21.

Shea, S. E. (2006). Mental retardation in children ages 6-16. Sem Ped Neurol 13:262-270.

Szymanski, L., and King, B. H. (1999). Practice parameters for the assessment and treatment of children, adolescents and adults with mental retardation and comorbid mental disorders. J Am Acad Child Adolesc Psychiatry 38:5S-31S.

Tallila, J.; Jakkula, E.; Peltonen, L.; Salonen, R.; Kestila, M.: Identification of CC2D2A as a Meckel syndrome gene adds an important piece to the ciliopathy puzzle. Am. J. Hum. Genet. 82: 1361-1367, 2008.

Uyguner O, Kayserili H, Li Y, Karaman B, Nurnberg G, Hennies H, Becker C, Nurnberg P, Basaran S, Apak M Y, Wollnik B.2007 A new locus for autosomal recessive non-syndromic mental retardation maps to 1p21.1-p13.3. Clin Genet. 71:212-219

URLs

PromoterInspector: http://www.genomatix.de

BLAST: http://www.ncbi.nlm.nih.gov/BLAST

UCSC: http://genome.ucsc.edu

SMART: http://smart.embl-heidelberg.de

PSORT: http://psort.ims.u-tokyo.ac.jp/cgi-bin/runpsort.pl

SOSUI: http://sosui.proteome.bio.tuat.ac.jp/sosuiframe0.html

COILS: http://www.ch.embnet.org/software/COILS_form-.html

Table 1. Linkage analysis of microsatellite markers across the 4p region. Markers shaded grey are within the homozygous critical region shared by the four affected individuals.

| Name | Physical Position (Mb) | Genetic Distance Female (cM) | Genetic Distance Male (cM) | Sex Averaged Genetic Distance (cM) | LOD |
|---|---|---|---|---|---|
| D4S1599 | 10.404 | 25.5 | 20.9 | 23.2 | -0.98979 |
| D4S3036 | 11.728 | 26.5 | 22.3 | 24.4 | -0.662288 |
| D4S403 | 13.259 | 28.7 | 23.4 | 26.05 | -1.479108 |
| D4S3048 | 15.516 | 29.7 | 28.8 | 29.25 | 2.304191 |
| D4S1525 | 16.092 | 29.7 | 29.9 | 29.8 | 2.208764 |
| D4S419 | 18.357 | 36.2 | 30.9 | 33.55 | 3.597317 |
| D4S1546 | 20.275 | 37.3 | 33.1 | 35.2 | 2.007724 |
| D4S425 | 23.165 | 38.3 | 34.1 | 36.2 | 2.822141 |
| D4S391 | 27.121 | 46.9 | 40.6 | 43.75 | -5.677216 |
| D4S2408 | 30.813 | 50.1 | 41.9 | 46 | -1.635551 |
| D4S405 | 39.947 | 69.4 | 44.8 | 57.1 | -1000 |
| D4S1592 | 57.276 | 91.6 | 48 | 69.8 | -1000 |

What is claimed is:

1. A method of screening a subject for a nucleotide sequence associated with mental retardation comprising:

a) isolating nucleic acid from a biological sample obtained from the subject and b) assaying nucleic acid from the sample for a nucleic acid encoding a protein comprising SEQ ID NO: 1 at the C-terminus, wherein the presence of the nucleic acid indicates that the subject has a nucleotide sequence associated with mental retardation.

2. The method of claim 1 wherein assaying comprises one or more hybridization assays, nucleotide sequencing, polymerase chain reactions (PCR) or any combination thereof.

3. The method of claim 1, wherein the nucleic acid comprises genomic DNA or RNA.

4. The method of claim 1, which is conducted using a kit comprising one or more of the following components:

a) a nucleotide sequence encoding a protein comprising an amino acid sequence that terminates in DHEGGSGMES (SEQ ID NO: 1) and that is associated with mental retardation;

b) a nucleic acid primer to amplify the nucleotide sequence of a);

c) a nucleic acid probe of between about 9 and 100 nucleotides that hybridizes to the nucleotide sequence encoding of a);

d) a reagent comprising a buffer, dATP, dTTP, dCTP, dGTP, a DNA polymerase, or a combination thereof;

e) instructions for assaying, diagnosing or determining the presence of the nucleotide sequence; and f) instructions for using any component or practicing the method.

5. The method of claim 1, wherein the nucleic acid encodes a protein consisting of SEQ ID NO:3.

6. A method of screening a biological sample from a subject for a mutant protein associated with mental retardation, the method comprising:

a) obtaining the biological sample from the subject; and b) assaying the sample for a protein that comprises SEQ ID NO:1 at the C-terminus thereof, wherein the presence of the protein indicates that the subject expresses a mutant protein associated with mental retardation.

7. The method of claim 6, which is conducted using a kit comprising one or more of the following components:

a) a protein comprising an amino acid sequence that terminates in DHEGGSGMES (SEQ ID NO:1) and that is associated with mental retardation, b) an antibody that selectively binds to the protein in a) but not to a CC2D2A-type protein that is not associated with mental retardation, c) a buffer;

d) instructions for assaying, diagnosing or determining the presence of the protein; and e) instructions for using any component or practicing the method.

8. The method of claim 6, wherein the protein is truncated at amino acid 779 or earlier.

9. The method of claim 6, wherein the protein has all or part of the C2 domain abolished.

10. A method of screening a biological sample from a subject for a gene sequence associated with mental retardation, the method comprising:

a) isolating nucleic acid from a biological sample obtained from the subject; and b) assaying the nucleic acid from the sample for one or more mutations in a nucleotide sequence encoding a CC2D2A protein, wherein the protein is defined by SEQ ID NO:7, wherein the presence of said one or more mutations results in premature truncation of the protein and abolishes all, or a part of, the C2 domain of the protein, and wherein the presence of the one or more mutations indicates that the subject has a gene sequence associated with mental retardation.

11. The method as defined in claim 10, wherein the one or more mutations are deletions, inversions, translocations, duplications, splice-donor site mutations, point-mutations or insertions.

12. The method of claim 10, wherein the one or more mutations occur in exon 19, or is a splice site mutation that results in the deletion of exon 19.

13. The method of claim 10, wherein the one or more mutations result in truncation of the CC2D2A protein at amino acid 779 or earlier.

14. The method of claim 13, wherein the one or more mutations result in a frameshift and add one or more non-wild-type amino acids, followed by a nonsense mutation.

15. The method of claim 10, which is conducted using a kit comprising one or more of the following components:

a) a nucleic acid primer to amplify a nucleotide sequence encoding a truncated version of the protein defined by SEQ ID NO:7 or a protein wherein all or part of the C2 domain is deleted;

b) a nucleic acid probe of between about 9 and 100 nucleotides that hybridizes to a nucleotide sequence encoding a truncated version of the protein defined by SEQ ID NO:7 or a protein wherein all or part of the C2 domain is deleted;

c) a reagent comprising buffer, dATP, dTTP, dCTP, dGTP, a DNA polymerase, or a combination thereof;

d) instructions for assaying, diagnosing or determining the presence of the nucleotide sequence; and e) instructions for using any component or practicing the method.

16. The method of claim 10, wherein the nucleic acid sequence encodes a protein comprising or consisting of SEQ ID NO:2, or SEQ ID NO:4.

17. The method of claim 10, wherein the protein is between about 80% and 100% identical to SEQ ID NO:3.

18. A method of screening a subject for a nucleotide sequence associated with Joubert Syndrome comprising:

a) isolating nucleic acid from a biological sample obtained from the subject; and b) assaying the nucleic acid from the sample for a nucleic acid encoding a protein comprising SEQ ID NO: 1 at the C-terminus, wherein the presence of the nucleic acid indicates that the subject has a nucleotide sequence associated with Joubert Syndrome.

19. The method of claim 18, which is conducted using a kit comprising one or more of the following components:

a) a nucleotide sequence encoding a protein comprising an amino acid sequence that terminates in DHEGGSGMES (SEQ ID NO:1) and that is associated with mental retardation;

b) a nucleic acid primer to amplify the nucleotide sequence of a);

c) a nucleic acid probe of between about 9 and 100 nucleotides that hybridizes to the nucleotide sequence encoding of a);

d) a reagents reagent comprising buffer, dATP, dTTP, dCTP, dGTP, a DNA polymerase, or a combination thereof e) instructions for assaying, diagnosing or determining the presence of the nucleotide sequence; and f) instructions for using any component or practicing the method.

20. A method of screening a biological sample from a subject for a mutant protein associated with Joubert Syndrome, the method comprising:

a) obtaining the biological sample from the subject; and b) assaying the sample for a protein that comprises SEQ ID NO:1 at the C-terminus thereof, wherein the presence of the protein indicates that the subject expresses a mutant protein associated with mental retardation.

21. A method of screening a biological sample from a subject for a gene sequence associated with Joubert Syndrome, the method comprising:

a) isolating nucleic acid from a biological sample obtained from the subject; and b) assaying the nucleic acid from the sample for one or more mutations in a nucleotide sequence encoding a CC2D2A protein, wherein the wild-type protein is defined by SEQ ID NO:7, wherein the presence of said one or more mutations results in premature truncation of the protein and abolishes all or a part of the C2 domain of the protein, and wherein the presence of the one or more mutations indicates that the subject has a gene sequence associated with mental retardation.

* * * * *

UNITED STATES PATENT AND TRADEMARK OFFICE

CERTIFICATE OF CORRECTION

PATENT NO. : 8,119,351 B2
APPLICATION NO. : 12/681347
DATED : February 21, 2012
INVENTOR(S) : Vincent et al.

It is certified that error appears in the above-identified patent and that said Letters Patent is hereby corrected as shown below:

Title Page:

Item (56) References Cited, OTHER PUBLICATIONS, please make the following changes:

Chelly J. et al. reference: change “Pathology” to -- Pathophysiology --.
Maria, Bernard L. et al. reference: change “583-590” to -- 581-591 --.
Molinari F. et al. reference: change “1179-1781” to -- 1779-1781 --.
Noor, A. et al. reference: change “CCD2A” to -- CC2D2A --.
Shea, S. reference: before “pp. 262-270” insert -- vol. 13, --.
Tallila, J. et al. reference: change “1362-1367” to -- 1361-1367 --.
Bernet, W. et al. reference: change “Retardaticn” to -- Retardation --.

Column 46:

Line 24 (claim 19, line 12), delete “reagents”.
Line 26 (claim 19, line 14), change “thereof” to -- thereof; --.

Signed and Sealed this
Third Day of April, 2012

David J. Kappos
*Director of the United States Patent and Trademark Office*